United States Patent [19]
Cameron, Sr. et al.

[11] Patent Number: 5,844,097
[45] Date of Patent: Dec. 1, 1998

[54] METHODS FOR THE DIAGNOSIS OF PERIPHERAL NERVE DAMAGE

[75] Inventors: Bruce M. Cameron, Sr., Houston, Tex.; Carl R. Merril, Rockville, Md.; Guy Joseph Creed, Arlington, Va.; Dale VanderPutten, Washington, D.C.

[73] Assignee: Monoclonetics International, Inc., Houston, Tex.

[21] Appl. No.: 475,345

[22] Filed: Jun. 7, 1995

Related U.S. Application Data

[60] Continuation-in-part of Ser. No. 242,980, May 16, 1994, Pat. No. 5,583,201, which is a division of Ser. No. 983,443, Dec. 1, 1992, Pat. No. 5,364,793, which is a continuation-in-part of Ser. No. 620,104, Nov. 30, 1990, abandoned.

[51] Int. Cl.$^6$ .............. C07K 16/00; C07K 1/00; C07K 14/00; C12P 21/08
[52] U.S. Cl. .................. 530/388.2; 530/359; 530/387.1; 530/388.1; 530/389.1; 435/7.1
[58] Field of Search .............. 435/7.1; 530/359, 530/387.1, 388.1, 388.2, 389.1

[56] References Cited

U.S. PATENT DOCUMENTS

| | | | |
|---|---|---|---|
| 3,540,850 | 11/1970 | Halpaap | 329/360 |
| 3,873,433 | 3/1975 | Seidel et al. | 204/462 |
| 3,930,983 | 1/1976 | Sieber | 436/516 |
| 3,979,507 | 9/1976 | Baker | 436/516 |
| 4,118,469 | 10/1978 | Caldwell et al. | 435/7.36 |
| 4,124,470 | 11/1978 | Dahms | 204/450 |
| 4,178,285 | 12/1979 | Felts et al. | 530/395 |
| 4,211,530 | 7/1980 | Goverde et al. | 436/536 |
| 4,264,589 | 4/1981 | Felts et al. | 530/392 |
| 4,311,788 | 1/1982 | Heuck et al. | 435/7.1 |
| 4,416,998 | 11/1983 | Adams et al. | 436/86 |
| 4,466,951 | 8/1984 | Pittman et al. | 424/1.17 |
| 4,468,466 | 8/1984 | Morrissey | 436/86 |
| 4,558,007 | 12/1985 | Anderson et al. | 435/26 |
| 4,579,735 | 4/1986 | Heimburger et al. | 424/530 |
| 4,579,825 | 4/1986 | Siedel et al. | 436/175 |
| 4,603,106 | 7/1986 | Cerami et al. | 435/5 |
| 4,619,895 | 10/1986 | Cubicciotti et al. | 435/792 |
| 4,645,748 | 2/1987 | Hurwitz et al. | 436/509 |
| 4,648,974 | 3/1987 | Rosskopf et al. | 210/651 |
| 4,654,301 | 3/1987 | Anderson et al. | 204/549 |
| 4,666,578 | 5/1987 | Yamamoto | 436/501 |
| 4,677,057 | 6/1987 | Curtiss et al. | 436/518 |
| 4,698,298 | 10/1987 | Dedieu et al. | 435/7.93 |
| 4,708,939 | 11/1987 | Siedel et al. | 436/13 |
| 4,722,893 | 2/1988 | Shigeta et al. | 435/7.94 |
| 4,746,605 | 5/1988 | Kerscher et al. | 435/7.1 |
| 4,772,549 | 9/1988 | Fiossare | 435/6 |
| 4,778,768 | 10/1988 | Heinegard et al. | |
| 4,791,066 | 12/1988 | Ishiguro | 436/516 |
| 4,820,505 | 4/1989 | Ginsberg et al. | 424/1.49 |
| 4,822,776 | 4/1989 | Cerami et al. | 514/21 |
| 4,828,986 | 5/1989 | Smith et al. | 435/7.94 |
| 4,877,746 | 10/1989 | Jansson et al. | 436/518 |
| 4,892,814 | 1/1990 | Harrington et al. | 435/5 |
| 4,892,815 | 1/1990 | Kerscher et al. | 435/7.1 |
| 4,895,558 | 1/1990 | Cham | 604/4 |
| 4,920,115 | 4/1990 | Nestler et al. | 514/178 |
| 4,923,439 | 5/1990 | Seidel et al. | 623/10 |
| 4,935,363 | 6/1990 | Brown et al. | 435/172.2 |
| 4,943,522 | 7/1990 | Eisinger et al. | 435/7.25 |
| 4,943,527 | 7/1990 | Protter et al. | 435/69.6 |
| 4,945,040 | 7/1990 | Fless et al. | 435/7.94 |
| 4,948,723 | 8/1990 | Hermon-Taylor et al. | 435/7.92 |
| 4,962,091 | 10/1990 | Eppstein et al. | 424/85.2 |
| 4,970,144 | 11/1990 | Fareed et al. | 435/5 |
| 4,973,638 | 11/1990 | Sparrow et al. | 526/303.1 |
| 4,975,528 | 12/1990 | Kaminski et al. | 530/359 |
| 4,978,503 | 12/1990 | Shanks et al. | 422/58 |
| 4,997,916 | 3/1991 | Aviv et al. | 530/399 |
| 5,030,722 | 7/1991 | Snyder et al. | 536/23.5 |
| 5,032,511 | 7/1991 | Takahashi et al. | 435/69.1 |
| 5,045,480 | 9/1991 | Johnson et al. | 436/532 |
| 5,049,488 | 9/1991 | Baer et al. | 435/6 |
| 5,055,396 | 10/1991 | Curtiss et al. | 435/7.93 |
| 5,059,528 | 10/1991 | Bollen et al. | 435/69.4 |
| 5,064,769 | 11/1991 | Gambert et al. | 436/516 |
| 5,089,602 | 2/1992 | Iskiker et al. | 530/359 |

FOREIGN PATENT DOCUMENTS

| | | |
|---|---|---|
| 0 257 788 | 3/1988 | European Pat. Off. . |
| 0 301 667 A1 | 2/1989 | European Pat. Off. . |
| 0 407 035 A2 | 1/1991 | European Pat. Off. . |
| 1 561 574 | 2/1980 | United Kingdom . |
| 2 208 317 | 3/1989 | United Kingdom . |
| WO90/04416 | 5/1990 | WIPO . |
| WO 90/12032 | 10/1990 | WIPO . |

OTHER PUBLICATIONS

Atlantic Antibodies, "Apolipoprotein E test kit", in The Medical Observer, vol. 21, p. 16, 1989.

VanderPutten et al, "Increased apolipoprotein–E concentrations in individuals suffering chronic low back syndrome identified by two–dimensional gel electrophoresis", Applied and Theoretical Electrophoresis, vol. 3, pp. 247–252, Oct. 13, 1993.

Carlsson et al, "Clinical relevance of the quantification of apolipoprotein E in cerebrospinal fluid" Clinica Chimica Acta, vol. 196, pp. 167–176, 1991.

Basu et al., Proc. Natl. Acad. Sci. USA, vol. 78, No. 12, pp. 7545–7549 Dec. 1981.

(List continued on next page.)

*Primary Examiner*—Lila Feisee
*Assistant Examiner*—Yvonne Eyler
*Attorney, Agent, or Firm*—Nikaido Marmelstein Murray & Oram LLP

[57] ABSTRACT

Methods of diagnosing peripheral nerve damage, including diagnosing and monitoring chronic back and cervical pain are disclosed. The methods involve subjecting a body fluid sample from a patient suspected of having chronic lumbar or cervical pain and peripheral nerve damage to two-dimensional electrophoresis or an immunoassay and measuring relative amounts of protein or proteins which increase or decrease in concentration as compared to a standard control. A preferred method employs an Apo-E variant as a marker of peripheral nerve damage. Also disclosed are kits for use with the diagnostic methods.

2 Claims, 27 Drawing Sheets

OTHER PUBLICATIONS

Basu et al., Science, vol. 219, Feb., 1983, pp. 871–873.
Boyles et al., J. Clin. Invest, vol. 76, Oct. 1985, 1501–1513.
Boyles et al., J. Clin. Invest, vol. 83, Mar. 1989, 1015–1031.
Boyles et al., J. Biol. Chem., vol. 265, No. 29, Oct., 1990, pp. 17805–17815.
Breslow, Ann. Rev. Biochem. 1985, 54:699–727.
Cuthbert et al., Proc. Natl. Acad. Sci. USA, vol. 81, pp. 4539–4543, Jul., 1984.
Elshourbagy et al., Proc. Natl. Acad. Sci. USA, vol. 82, pp. 203–207, Jan., 1985.
Folkman et al., Nature, vol. 273, Jun. 1, 1978 pp. 345–349.
Frohlich et al., Clin. Biohem., vol. 22, pp. 51–56, 1989.
Hallman et al., Am. J. Hum. Genet. 49:338–349, 1991.
Kostner, Biochemical Society Transactions, 629th Meeting, London, vol. 17, pp. 639–641.
Lalazar et al., J. Biol. Chem., vol. 264, No. 15, May 25, 1989, pp. 8447–8450.
Mahley, Science, vol. 240, Apr. 1988, pp. 622–630.
Majack et al., J. Cell. Biol., vol. 107, Sep. 1988, 1207–1213.
Menzel et al., Electrophoresis 1986, 7, 492–495.
Muller et al., Journal of Neuroscience Research 18:222:229 (1987).
Pitas, J. Biol. Chem, vol. 262, No. 29, Oct. 15, 1987, pp. 14352–14360.
Pitas et al., Biochimica et Biophysica Acta 917 (1987) 148–161.
Rall, Jr. et al., J. Clin. Invest., vol. 83, Apr. 1989, pp. 1095–1101.
Roheim et al., Proc. Natl. Acad. Sci. USA, vol. 76, No. 9, pp. 4646–4649 Sep., 1979.
Roheim et al., European Heart Journal (1990) 11 (Supplement E), 225–229.
Ross, The New England Journal of Medicine, vol., 314, No. 8, Feb. 20, 1986, pp. 488–500.
Snipes et al., Proc Natl. Acad. Sci. USA, vol. 83, pp. 1130–1134, Feb., 1986, Neurobiology.
Sprecher et al., Clin. Chem. 30/12, 2084–2092 (1984).
Utermann et al., J. Lipid Research, vol. 25, 1984, pp. 378–382.
Weisgraber et al., J. Biol. Chem., vol. 257, No. 5, Mar. 10, 1982, pp. 2518–2521.
Weisgraber et al., Biochemical and Biophysical Research Communications, vol., 157, No. 3, 1988, pp. 1212–1217.
Werb et al., J. Exp. Med., vol. 158, Oct., 1983, pp. 1272–1293.
Wilson et al., Science, vol. 252, Jun. 28, 1991, pp. 1817–1822.
Zannis et al., Biochemistry, vol. 20, No. 4, 1981, pp. 1033–1041.
Zannis et al., J. Lipid Research, vol. 23, 1982, pp. 911–914.
Ahonen et al., Acta Neurologica Scandinavica, vol. 58, Fasc. 6 (1978) 358–365.
Felgenhauer et al., Clinica Chimica Acta, 100 (1980) pp. 121–132.
Frot et al., *Marker Proteins in Inflammation*, pp. 253–273 (1982).
Harrington et al., Clin. Chem. vol. 30, No. 12, pp. 1933–1937 (1982).
Kushner, *Annals of the New York Acad. of Sci.*, pp. 39–48 (1982).
McCarty, *Annals of the New York Acad. of Sci.*, pp. 1–10 (1982).
Merril et al., Clin. Chem. vol. 28, No. 4, pp. 1015–1020 (1982).
Tracy et al., Clin. Chem. vol. 28, No. 4, pp. 890–899 (1982).
Tracy et al., Clin. Chem. vol. 28, No. 4, pp. 900–907 (1982).
Tracy et al., Clin. Chem. vol. 28, No. 4, pp. 915–919 (1982).
Tracy et al., J. Clin. Laboratory Automation, vol. 3, No. 4, (1983) pp. 235–243.
Varma et al., Experimental Cell Research 173 (1987) pp. 163–173.
Willard et al., Clin. Chem. vol. 28, No. 4, pp. 1067–1073 (1982).
Havel et al., "Lipoproteins and Lipid Transport" in *Metabolic Control and Diseases*, pp. 393–494 (1980).
Hui et al., J. Biol. Chem., pp. 11775–11781 (1980).
Hochstrasser et al., Applied & Theoretical Electro., pp. 73–76 (1988).
Ignatius et al., Science, vol. 236, pp. 959–962 (1987).
Ignatius et al., PNAS USA, vol. 83, pp. 1125–1129 (1986).
Ignatius et al., Prog. in Brain Res., vol. 71, pp. 177–184 (1987).
Carlsson, et al., *Clinica Chimica Acta*, "Clinical relevance of the gantification of apoliprotein E in cerebrospinal fluid", vol. 196, (1991) pp. 167–176.
Harrel, et al., *Biochem. BIophys. Aeta*, 573:175–183, 1979.
Horie, et al., The Functional Characteristics of Human Apolipoprotein F. Variant (Cysteine at Residue 142), May Explain Its Association with Dominant Expression of Type III Hyperlipoprotemia, JBC 267 (3) 1962–1968 (1992).
Lettimaki, et al., Association of Apolipoprotein E and B Polymorphism w/Serum Lipids, Ann. Med., 23:657–662 1991.
Xhignesse, et al., Influence as of Common Variants of Apol–protein E on on Measures of Lipid Metabolis in a Sample Selected for Health, Arteriosclter. Thromb. 11(4):1100–1110 (1991).

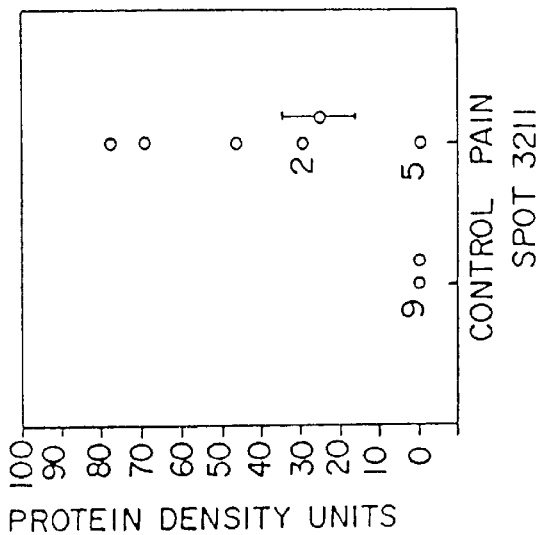
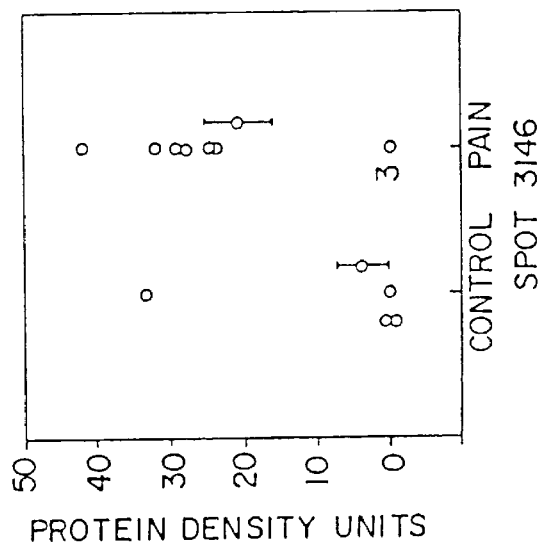
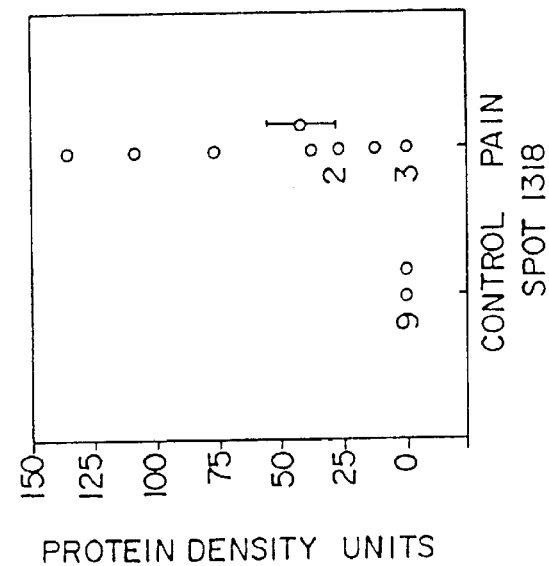

X = UNKNOWN AMINO ACID

SPOT 719 N-Term  x|VEQAVETEPE|xEL
Apo E N-Term      GCQAKVEQAVETEPEPELRQQTEW
                           30              40

METHODS FOR THE DIAGNOSIS OF PERIPHERAL NERVE DAMAGE

This application is a continuation-in-part of U.S. Ser. No. 08/242,980, filed May 16, 1994 issued as U.S. Pat. No. 5,583,201 and, which is a divisional of U.S. Ser. No. 07/983,443, filed on Dec. 1, 1992, issued as U.S. Pat. No. 5,364,793 which is a continuation-in-part of PCT application Ser. No. PCT/US91/08552, filed Nov. 15, 1991, which is a continuation-in-part of U.S. Ser. No. 07/620,104, filed Nov. 30, 1990 now abandoned.

FIELD OF THE INVENTION

This invention relates to novel methods for the diagnosis of peripheral nerve damage, including that damage which causes back and neck pain, particularly chronic back and neck pain.

BACKGROUND OF THE INVENTION

Conditions which cause pain are obviously very prevalent in medicine. Very often, the cause of the pain is apparent. However, frequently, the physiological cause of the pain is not known. It is, of course, important to the clinician to determine the cause of the pain, so that proper treatment can be instituted. Prime examples of painful conditions wherein it is difficult to determine the cause of the pain are in patients experiencing spinal pain (i.e, lumbar, thoracic and cervical), particularly lower back ache or neck pain, and more particularly chronic cases. It is crucial in these conditions to determine whether they are caused by muscle or fibrous tissue injury, or are actually a result of nerve damage. The proper determination of the etiology will guide the clinician in the proper form of treatment.

Eighty-five percent of the United States population, at one time or another, seek medical consultation for back ache, particularly chronic back ache. Over 40 million people claim disability due to chronic back pain (or low back syndrome) and the medical costs alone to care for this group is over 40 billion dollars [Aronoff, G. M., *Evaluation and Treatment of Chronic Pain*, Urban and Schwarzenberg, Baltimore (1985)]. This does not include the enormous socio-economic loss, estimated to be in the trillions of dollars. In 1985, 2.7 million individuals received social security disability insurance at a overall cost of $ 18.9 billion [Social Security Administration, *Report of the Commission on Evaluation of Pain*, Washington D.C., Department of Health and Human Services (1986)].

Clinically, chronic pain, as opposed to acute pain, is continuous pain which persists for six months or more. Pain has been defined as an unpleasant sensory and emotional experience associated with actual or potential tissue damage, or described in terms of such damage [*International Association for the Study of Pain*, chaired by Mersky (1979)]. Vasudevan has noted that there are several aspects to pain: nociception (the perception of pain, a physical stimulus); interpretation of the stimuli as "painful"; and the evaluation of the pain as creating suffering. [Vasudevan et al., "Counseling the Patient with Chronic Pain—The Role of the Physician", In *Persistent Pain*, Kluwer Academic Publishers, Boston (1988)].

In the present state of the art, there is no objective, accurate test for spinal pain, particularly chronic lower back (or lumbar) pain (hereinafter referred to as "CLP" which stands for "chronic lumbar pain") and/or radiating pain, and chronic cervical (neck) pain (hereinafter referred to as "CCP" which stands for "chronic cervical pain"). More specifically, there is no protein-based clinical test which quantitatively detects the presence or absence of CLP or CCP, much less one having the capability to quantitate or monitor the progression or regression of CLP or CCP. The existence of such a test would be of infinite value to the patient, the doctor, and the society which bears the cost-burden of this problem (i.e., insurance companies and government health and social security departments). An objective test for CCP or CLP would allow for the following:

1. Verify the presence or absence of the syndromes of CCP or CLP based on an organic cause. Ideally, this test would be performed on the first visit so that a baseline could be established to take advantage of the quantitative aspects of the test. If no organic cause existed, according to the test, then it would not be necessary to proceed with the more costly examinations (e.r., MRI's, CT scans, myelograms, discograms, bone scans, electromyelograms, and consultations) which are, in the present state of the art, required to rule out causes for this syndrome. If an organic cause is determined to exist, then the routine work-up could proceed with high expectations for success. At this point, if the routine tests for CLP or CCP are negative and the protein-based analysis disclosed herein is positive for back syndrome, then the treating physician would be justified in continuing to seek a correctable, organic cause.

2. Monitor the progress and effectiveness of treatment. All chronic back or cervical syndromes are treated conservatively, initially. The effect of this treatment could be assayed and one or more of the following judgments could be made: continue with an improving test; discontinue with a worsening test; change treatment with a worsening test; recommend initial or revision surgery only when the test was worsening or not showing any improvement. Thus, an objective, biochemical test would increase the efficiency of conservative patient management and eliminate any unnecessary surgery. It is foreseeable that the test disclosed herein would become the standard for assessment, wherein surgery would be indicated only if the protein analysis indicated it.

3. Identify the point of maximal medical improvement. By periodically administering the test during a course of treatment, the quantitative characteristic of the test would allow the physician to assess the degree of the symptoms of peripheral nerve damage of backache and/or radiating pain (particularly radiculopathy, which is currently thought to be due to nerve root damage) (CLP) and CCP and assist him in identifying the point where medical treatment should cease. At this point, treatment and rehabilitation efforts can stop and the physician, patient, and employer can feel comfortable with a recommendation to return to full-time work, limited work, settle claims, retirement, etc. Medical costs should be reduced while the efficacy of medical treatment improves.

4. Identify those patients who are suffering disability from the pain of CLP or CCP from those who are not suffering from the pain of neck pain, backache and/or radiating pain. (Radiating pain is defined as pain that is perceived in one or both buttocks and/or one or both lower extremities. Radiating pain is currently divided into two categories: (1) referred pain which means pain that radiates into the buttock(s) and thighs and remains above the knee; and (2) radiculopathy which means pain which radiates into the buttock(s), thigh and below the knee, sometimes to the foot. Referred pain may be due to muscles, fascia, etc., while radiculopathy is thought to be due to nerve root damage.) This will assist the proper authorities in placing those who qualify for financial assistance because of an objectively documented back pain condition in the appropriate social program, and to identify and remove those who do not medically qualify.

5. Aid the courts and others concerned with assessing correctly the compensable damages of pain and suffering secondary to neck pain, backache and/or radiating pain.

An objective test for peripheral nerve damage, in general, would allow the clinician to verify whether patients with peripheral nerve problems with neurological symptoms (for example: carpal-tunnel syndrome; brachial plexus problems; thoracic outlet syndrome; peripheral nerve injuries; peripheral nerve damage as a result of disease, ageing, congenital abnormalities neoplasms; optic or auditory nerve damage due to many conditions, etc.) suffer from nerve damage, which would dictate a particular course of therapy.

Clinical tests for CCP or CLP include inspection, palpitation and manipulation. The vast majority of clinical tests depends upon the patient reporting a painful or other type of response, and are therefore unreliably subjective. Objective clinical tests in the current state of the art include reflex changes, spasm and properly performed straight leg raising tests, and may or may not aid in the diagnosis of lower back syndrome. Moreover, they neither quantitate nor monitor the progression of lower back syndrome.

Thermograms, psychological interviews (e.g., McGill and MMPI tests), polygraphs and instrumentation tests may also be used to assist in the diagnosis of CLP and CCP. However, none of these is completely accurate because they are also subjective and depend on the patient reporting the type and degree of response sustained.

Laboratory tests such as X-rays, CT scans, MRI's, myelograms, discograms, EMG's and bone scans can only delineate the presence or absence of possible pain-producing lesions which must then be correlated with the clinical findings of CLP or CCP. They do not detect the presence or absence of CLP or CCP per se, nor in any way quantitate them. Further, it is not uncommon to have false positive and false negative results with these tests (reported rates of error of about 20–50%). All or any of these tests may be negative and the patient may continue to complain; on the contrary, all or any of these tests may be positive and a patient may remain asymptomatic. Moreover, not only are these tests expensive, some of these tests expose the patient to unnecessary radiation.

The capacity to obtain diagnostic information from proteins, particularly blood proteins, has progressed rapidly since the middle of the 19th century when it was believed that serum contained but a single protein, albumin. By 1887, Lewith had demonstrated, by salt precipitation, that serum proteins could be separated into the albumins and globulins. The ratio of albumin to globulin (A/G ratio) was shown to have diagnostic value and is still in use today. With the introduction of electrophoretic separations, immunoanalytic techniques and enzymatic assays, the number of plasma proteins of diagnostic value has grown exponentially. The examination of specific blood proteins has proven to be an invaluable diagnostic aid, as in the monitoring of creatine phosphatase levels in determining cardiac damage following a myocardial infarct. The increased resolution and detection of plasma proteins with two-dimensional electrophoresis [O'Farrell, *J. Biol. Chem.*, Vol. 250, pp. 4007–4021 (1975)] combined with silver-staining [Merril, *Proc. Natl. Acad. Sci., USA*, Vol. 76, pp. 4335–4339(1979)] allows investigators an examination of over one thousand proteins in human plasma and approximately 300 proteins in human cerebrospinal fluid.

Anderson et al. [*Proc. Natl. Acad. Sci., USA*, Vol. 74, pp. 5421–5425 (1977)] initiated the mapping and the identification of the plasma proteins resolved by two-dimensional electrophoresis. The goal of this work was to use these proteins for screening genetic variants. By 1984, they were able to identify only 38 of 646 serum proteins visualized by their electrophoretic and staining systems [Anderson et al., *Plasma Proteins*, Vol. IV, pp. 221–269, Academic Press, New York (1984)].

It has been suggested that two-dimensional gel electrophoresis can be used to correlate the presence of a protein in serum or tissue, or an increase in its amount, with various diseases [Tracy et al., "Two-Dimensional Gel Electrophoresis: Methods and Potential Applications in the Clinical Laboratory", *J. Clin. Lab. Autom.*, Vol. 3, No. 4, p. 235 (1983)]. It has also been noted that development of a protein "profile" for disease states may be useful in diagnosis [Tracy et al., supra at 242].

However, the increase in resolution provided by two-dimensional electrophoretic techniques and the increased detection available with recently developed staining methods has not yet resulted in widespread clinical applications of this methodology. Thus, the diagnoses of disease states in general, and chronic back pain in particular, by way of two-dimensional gel analysis is new, there being only one such reported method. This method utilizes two-dimensional gel protein analysis of cerebrospinal fluid to distinguish Creutzfeldt-Jakob disease from other causes of dementia [Harrington et al., U.S. Pat. No. 4,892,814].

Harrington et al. [*Clinical Chem.*, Vol. 31, pp. 722–726 (1985)] also found some proteins associated with Parkinson's disease and schizophrenia, which may or may not be of diagnostic value. Some proteins mapped and identified by two-dimensional electrophoresis of plasma [Anderson et al., 1984, supra] and cerebrospinal fluid [Goldman et al., *Clin. Chem.*, Vol. 26, pp. 1317–1322 (1980)] have demonstrated to be polymorphic and thus may provide for genetic and forensic applications, but have not proven reliable as diagnostic markers for particular diseases.

To overcome the aforementioned deficiencies in the art, the present inventors have developed an objective, quantitative test for diagnosing peripheral nerve damage, particularly that which causes spinal pain and more particularly CLP or CCP. The test utilizes two-dimensional electrophoresis to analyze the increased or decreased concentrations of certain proteins in a body fluid sample from a patient as compared to a normal control. During the course of developing this test, the present inventors discovered a protein marker, which is indicative of peripheral nerve damage.

BRIEF SUMMARY OF THE INVENTION

It is an object of the present invention to provide for an objective, diagnostic test for peripheral nerve damage, particularly that which causes chronic spinal pain, and more particularly chronic lower back and neck pain. As used herein, "peripheral nerve damage" refers to all peripheral nerve problems with neurological symptoms (for example: cubital or carpal-tunnel syndrome; brachial plexus problems; thoracic outlet syndrome; peripheral nerve injuries; peripheral nerve damage as a result of disease, ageing, congenital abnormalities, neoplasms; optic or auditory nerve damage due to mian48y conditions; conditions involving the autonomic nerve system; etc.).

It is a further object of this invention to provide a method for determining the severity of the peripheral nerve damage, particularly that which causes chronic spinal pain and more particularly CLP or CCP.

It is yet a further object of this invention to provide for a method of determining the type (i.e., conservative versus surgery) and the effectiveness of a course of treatment for conditions resulting from peripheral nerve damage, particularly that which causes spinal pain and more particularly chronic lower back or cervical pain.

In the course of developing the foregoing objects, the present inventors have also identified proteins associated with CCP and CLP according to their migration on two-dimensional polyacrylamide gels. Thus, the so-identified proteins and products derivable therefrom (for example, antibodies) are also part of the present invention. As one skilled in the art would recognize, a spot on a stained two-dimensional gel could represent one or more proteins.

A number of proteins detectable by the methods of the present invention have been found to be altered in concentration and/or migration pattern. As would be expected in studies of this nature, some protein spots have been found to be of a higher diagnostic value than others when subjected to statistical analysis.

According to an initial study of the present invention, chronic lower back pain is accurately diagnosed by the detection of increased or decreased levels of forty-four proteins in patients suspected of suffering from chronic back pain as compared with normal controls (i.e., normal volunteers with no clinical evidence of chronic back pain). In patients with chronic back pain, 29 proteins are found to be increased to levels at least three-fold as compared to normal controls, with statistical significance. (Statistical significance is defined herein as a p value of less than or equal to 0.05 by the Student t test or the log Student t test.) Of these 29 proteins, 13 are found to only occur in chronic back pain patients. On the other hand, patients with CLP exhibit decreased levels of at least three-fold of 13 proteins as compared to controls. Seven of these proteins are totally absent in patients with the back pain syndrome. A further investigative study ("second study") found one additional spot which has vern high predictability of the presence or absence of CCP and CLP and, thus, is favored for diagnostic value, as well as ease of observation.

Thus, the diagnostic methods of the present invention can employ techniques to identify the increase or decrease, or presence or absence, of these proteins in a sample to diagnose CLP or CCP. Of course, the presence or absence of a defined protein or proteins in a spot in a specific location on the gel may be due to changes in the migration of proteins altered in charge or molecular weight. Also, one may perform multivariate analyses on an array of more than one of the proteins by usual statistical methods.

These proteins are identified by their relative molecular weight and isaelectric point (i.e., their migration on two-dimensional electrophoresis gels). The exact identity of only one of the proteins is known (spot 1bp13–14.719). However, as CLP and CCP may be associated with inflammation, some of the proteins which appear to be increased in CLP and CCP may belong to the class of plasma proteins which are known to be increased in response to tissue injury and disease. Tlis class of proteins was first discovered by the observation of their induction in patients with pneumococcus pneumonia [MacCarty, M , "Historical Perspective on C-Reactive Protein." In Kushner et al. (Eds.,) *C-Reactive Protein and the Plasma Protein Response to Iniury*, Annals of the New York Academy of Sciences, Vol. 389, pp. 1–10 (1982)]. Since these initial observations, the metabolic and physiological changes that occur in the acute phase response have been studied in numerous laboratories. It has been found that the acute phase response may be invoked by many different types of stimuli, such as trauma, infections, noninfectious inflammatory states, and tissue infarctions. See, Kushner et al. (Eds.), supra. While it is known that most of these proteins are synthesized in the liver, the nature of their induction is not yet known. Induction could be by blood borne substances or by neuronal factors since there are both blood vessels and nerves in the region of synthesis, the hepatic lobes [MacIntyre et al., "Biosynthesis of C-Reactive Protein." In Kushner et al. (Eds.), sunra, pp. 76–87].

Some of the acute phase response proteins have been induced in mice, and their relative positions have been identified with two-dimensional electrophoresis [Pluschke et al., *Clin. Exp. Immunology*, Vol. 66, pp. 331–339 (1986)]. The present applicants could not be sure that the proteins affected in the present invention are the previously observed acute phase response proteins or, perhaps, new members of this class of response proteins. However, the applicants sent an aliquot from each of the clinical samples to a commercial laboratory for measurement of complement C3, alpha-1 antitrypsin, transferrin, alpha-1 acidic glycoprotein, and C-reactive protein (some of the well characterized acute phase response proteins). No elevation of these proteins could be detected by standard assays.

One of the markers found in the present invention to be a highly predictable marker of CLP or CCP is the spot referred to as 1bp13–14.719 (or sometimes referred to herein as "719"). The present inventors focused on this particular marker, and further investigations revealed that this spot is actually an apolipoprotein E variant. It is documented in the art that apolipoproteins accumulate markedly in the area immediately local to the nerve tissue during the regeneration of damaged peripheral nerves (less in the regeneration of damage to the CNS). This led the present inventors to investigate whether peripheral nerve damage, in general, would show increased amounts of spot 719 in the plasma of patients with peripheral nerve damage other than that nerve damage which causes CLP and CCP. As disclosed in the present application, positive results for the increase of the apo-E variant were seen in patients with other types of peripheral nerve damage. It should also be noted that iclcl-eases in the density of spot 719 can be seen with the naked eye on two-dimensional gels, without the need for computer scanning densitometry. When quantitative measurements of density are measured, this spot 719 is about five-fold (can range from 2 to 5-fold) greater in spot density in peripheral nerve damage of patients as compared to normal controls.

Based on the data obtained by the present inventors in this application in connection with chronic conditions, and in view of the contemporary knowledge of nerve damage in the literature, it is contemplated that the methods of the present invention can be used to diagnose peripheral nerve damage at any time after injury to the nerve has occurred (i.e., in the acute phase as well as the chronic phase), particularly with respect to the observation of spot 719 (the apo-E variant).

It is unlikely that the protein changes noted herein are due to drugs, such as those the patients may have taken to alleviate their pain, since three of the patients in the initial study were not taking any medication for their chronic back pain. These three patients displayed protein alterations that were similar to those taking medication. It is also unlikely that the protein changes are artifacts of storage. Tracy et al. demonstrated the occurrence of plasma proteins which are altered by freezing and storage at −20° C. [Tracy et al., *Clin. Chem.*, Vol. 28, pp. 890–899 (1982)]. Our spots 1305, 1318, 1323 and 4614 are in the region noted for the appearance of such spots by Tracy et al. However, as the patient and the age and sex matched control samples were drawn at the same time and stored under identical conditions, it is unlikely that the proteins of interest in this study are storage artifacts.

The methods of the present invention include one of particularly significance. That is, the present inventors have developed a plasma test for peripheral nerve damage and repair by focusing their attention on the apo-E variant of spot 719. Secondarily, this discovery leads to a plasma test for spinal pain and other pain due to nerve damage. Consequently, the present inventors have discovered a plasma test for pain. In other words, peripheral nerve damage can produce spinal pain (and/or other neurological deficits) and pain (and/or other neurological deficits) outside the spinal column. Peripheral nerve damage can be diagnosed by the presence of an increase in the apo-E variant (spot 719) in the plasma. Therefore, spinal pain (and/or other neurological deficits) and pain (and/or other neurological deficits) outside the spinal column can be diagnosed by an increase in the plasma apo-E variant.

DESCRIPTION OF THE DRAWINGS

FIG. 4: A scatter diagram illustrating proteins which showed moderately robust correlations with chronic back pain in the initial study. The numbers to the left of a circle indicate the frequency greater than 1 that a patient with that value was observed. The circle and bar to the right of each group of data indicate the mean and the standard error of the mean for that group.

FIG. 24a shows the location of spots other than spot 719 (such as other apolipoproteins and some acute phase reactant proteins). See further the legend on FIG. 25a for description of spot numbers. FIG. 24b is a 2-D gel of a patient with CLP; the boxed area is enlarged in the lower, right-hand corner of the figure. FIG. 24c is a 2-D gel of a normal control showing a much-diminished, barely-visible spot 719; as with FIG. 24b, the lower, right-hand corner of the figure is an enlarged view of the boxed area.

DETAILED DESCRIPTION OF THE INVENTION

Figure 1:
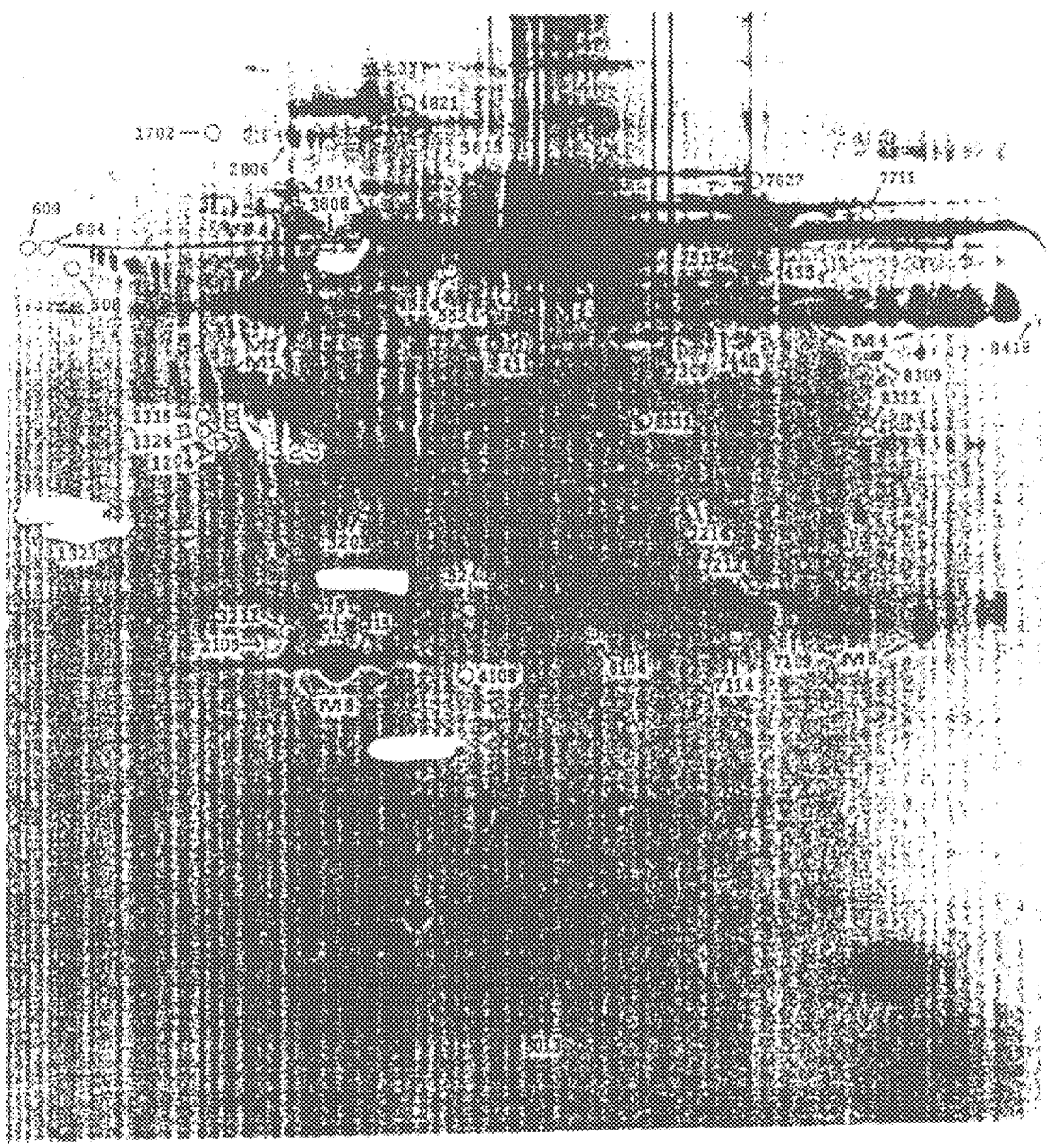
FIG. 1: Plasma gel stained with silver. This gel was made with 1.47 ul of plasma from a control. Circles mark proteins not generally visible in controls but present in patients with chronic back pain. Numbers preceded by 'M' designate landmarking proteins identified in Table I. The remaining labeled proteins are those which either increased or decreased by a factor of three or more and were statistically significant, as indicated in Tables II and III.

This invention involves methods of diagnosing peripheral nerve damage, particularly that which causes spinal pain, and more particularly CLP and CCP wherein protein samples from both normal and abnormal individuals are subject to electrophoresis and/or immunoassays. In the case of two-dimensional gel electrophoresis, a large number of protein spots common to both types of individuals and spots which appear or disappear in the abnormal patient group are determined. Initially, the number of protein spots to be examined is reduced to only those showing statistically significant differences between normal controls and patients with chronic back pain. This is determined by performing a Student's t test or a log Student's t test on the spot intensity data. Those proteins that have statistical differences at a significance level of 0.05 on either or both of these tests are chosen for further study. In addition, the present invention also contemplates the use of one-dimensional electrophoresis.

CLP has been shown to arise from trauma to spinal nerve roots [Schonstrom, N. et al., *Spine*, Vol. 9, pp. 604–607 (1984)]. While it is difficult to examine biochemical alterations in human nerve injuries, molecular changes associated with nerve root damage have been studied in several animal models. [Ignatius, M. J., *Progress in Brain Research*, Vol. 71, pp. 177–184 (1987)]. Changes in the injured nerve include elevation in the local concentrations of acute phase reactant proteins, infiltration by circulating monocytes, increased levels of protein synthesis and increases in apolipoprotein concentrations. One of the most striking physiological differences in these animal models of nerve damage is a 250-fold increase in the local concentration of apolipoprotein E (apo-E), with sciatic nerve crush injuries [Skene, J.H.P, Proc Natl. Acad. Sci. USA, Vol. 80, pp. 4169–4173

(1983)]. This nerve damage-associated elevation in the area surrounding the nerve correlates with the present inventors' finding that a subset of the apolipoprotein E complex of spots in our 2-D gels was increased greater than five-fold in the plasma of individuals suffering CLP and CCP. Other apolipoproteins and acute phase reactants that might be expected to be elevated in plasma of individuals suffering nerve root damage, based on the animal studies, (most notably apo-D, apo-AI and apo-AIV) were identified by their 2-D gel location, but were found not to be elevated to a statistically significant degree in our analysis. To better understand the appearance of the apolipoprotein E variant (spot 719), the present inventors wish to determine the following: (1) was pain required for the protein change or was only a biomechanical abnormality necessary?; (2) was it limited to the lumbar region or did it apply to the whole spine?; (3) was it present in all individuals with acute or chronic pain?; (4) was it found in cases of peripheral nerve damage?; and (5) was it associated with an inflammatory response? To help answer these questions, the present inventors also analyzed the plasma of patients suffering from a variety of other chronic and acute painful conditions, as well as patients that had recovered from CLP and individuals with chronic inflammatory conditions. Based on this analysis and previously-reported observations, the present inventors proposed that the apo-E abnormality results from a chronic inflammatory insult, causing continuous attempts to regenerate damaged nerve. Further, although other investigators have documented that the concentration of apo-E immediately surrounding the damaged nerve tissue increases greatly, none of the prior art discloses or suggests that an increase in apo-E in the plasma, in general, and human plasma, in particular, would also occur.

Figure 25A:
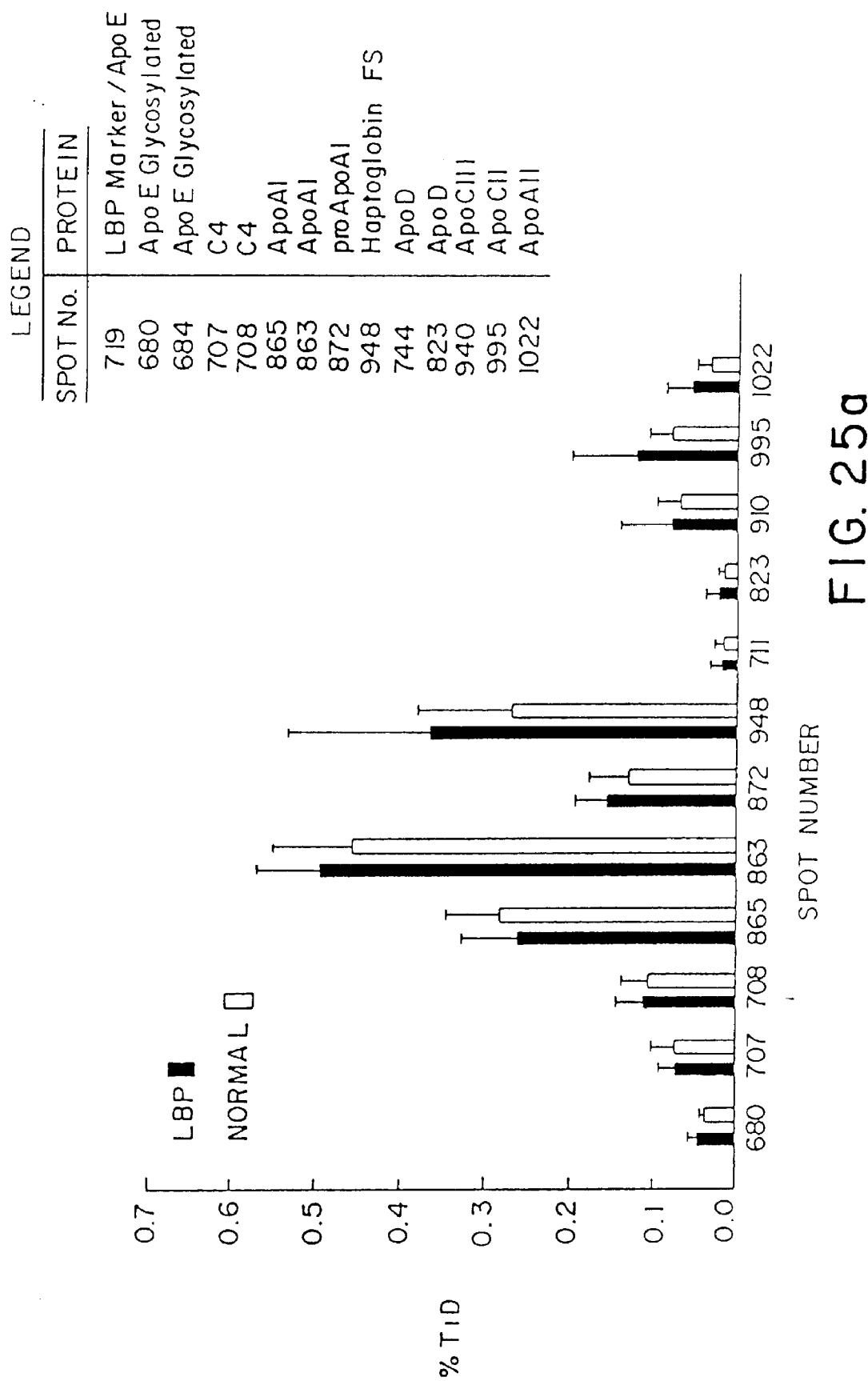
FIGS. 25a and b: This set of figures are bar graphs comparing the measured density [% TID (or total integrated density)] of the spots shown in FIGS. 24a–c between chronic lower back pain patients and normal controls. While there are observed increases in the other apolipoproteins, these have not been proven to be as statistically significant as spot 719 (apo-E variant).
Figures 25B, 27:
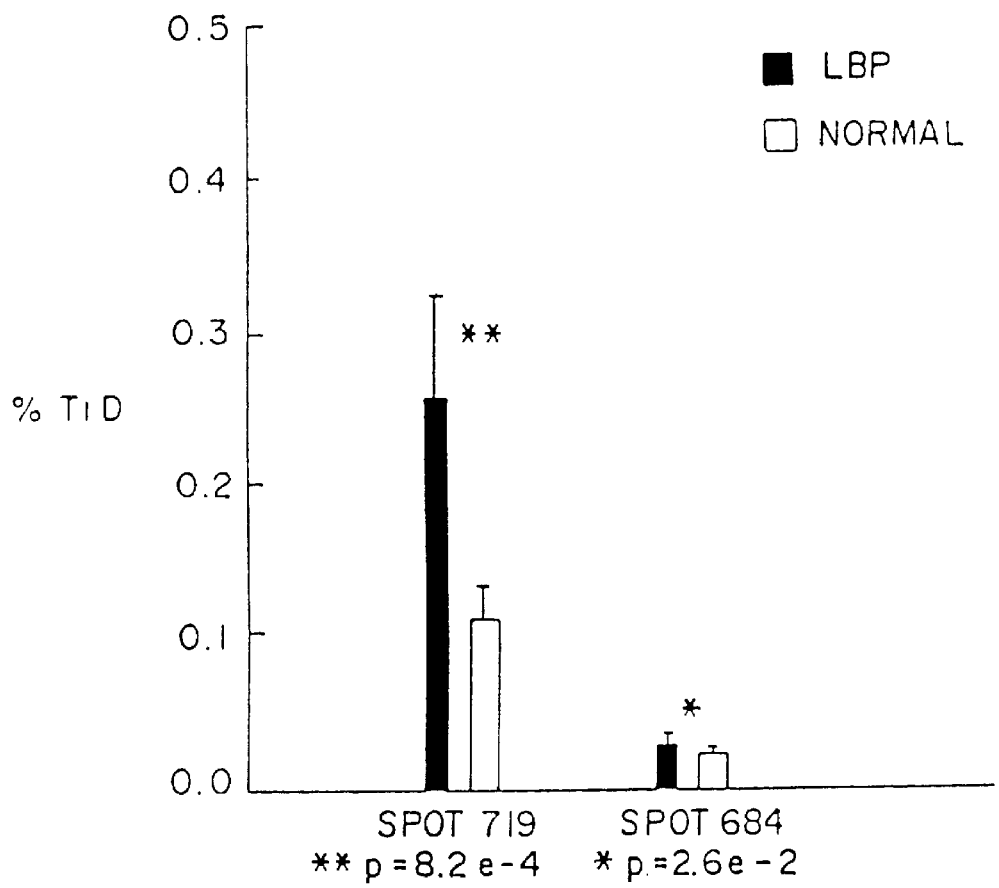
FIG. 27: N-terminal sequence analysis of spot 719 protein. There is 100% homology with the known N-terminal sequence of plasma apo-E.
Figure 26:
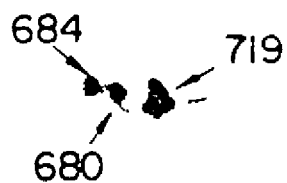
FIG. 26: Immunoblot prepared in accordance with the example in the present invention, showing spot 719 is positive for anti-apo-E reactivity. The other positive spots (680 and 684), other forms of apo-E, were also analyzed for quantitative variations correlating with CLP, but there was no significant correlation (see FIGS. 25a and b).

In order to better understand the reason for increased concentration of spot 719 in the present studies, the present inventors undertook to identify the protein comprising this spot. Two-dimensional gel maps of plasma proteins were used to locate spot 719 in the area of the two-dimensional gel, which contains transthyretin ("TTR") dimer and the apo-E complex of spots. Spot 719 appears to have a relative molecular weight of about 32–36 kD and a pI of about 6.0–6.2 as determined from the 2-D gels. Immunoblot analysis of the two-dimensional gel showed strong reactivity of spot 719 within the apo-E monoclonal antibody (FIG. 26). N-terminal microsequence analysis was performed to confirm the identity of spot 719 as apo-E (FIG. 27). In addition, microsequence analysis independently verified the identity of another spot in the region not related to lower back pain as TTR. Circulating plasma apo-E is active in lipid transport from the gastrointestinal system to the periphery through the plasma. In addition to this endocrine function, apo-E also has paracrine and autocrine activities for cholesterol redistribution. It has also been shown to be a regulator of the immune response and a neurotropic factor. The paracrine activity of apo-E in nerve regeneration has been well described in sciatic nerve crush in rats [Schubert, D. et al., J. Cell Biol., Vol. 104, pp. 635–642 (1987)]. In experimental models, by three weeks after nerve injury as much as five percent of the total soluble protein of the nerve is apo-E [Mahley, R. W. et al., Science, Vol. 240, pp. 622–630 (1988)]. While in the CNS, there are similar levels of apo-E synthesis in response to injury, response to accumulation around the tissue is not observed [Muller, H. W. et al, Science, Vol. 228, pp. 499–501 (1985)]. It has been suggested that the lack of accumulation of apo-E in the CNS is an important factor in the lack of regeneration of neurons in the brain.

The source of the apo-E comprising spot no. 719 is not obvious. The blood nerve barrier in the dorsal root ganglion and other nerve roots has been shown to be compromised by nerve crush injury. [Howe, J. F. et al, Pain, Vol. 3, pp. 25–41 (1977); and Wiesel, S. W. et al, Spine, Vol. 10, pp. 549–551 (1984)]. This may lead to proteins entering the circulation at the point of injury, although this is mere speculation. The extraordinary amount of paracrine apo-E that can enter the circulation at the site of injury may account for the observed increase of this polypeptide in the plasma. However, it is very noteworthy that elevated levels of the other apolipoproteins observed in the literature (e.g., apo-D, apo-AI and apo-AIV) to accumulate in the local area around the nerve tissue do not correlate with statistically significant increases in levels in the plasma, as the present inventors have observed with the apo-E of spot 719.

It is also possible that the source of increased apo-E in the plasma of individuals with CLP or CCP is endocrine and produced in response to acute phase reactants resulting from the injury. However, the levels of the few acute phase reactants whose locations can be determined on 2-D gels do not differ between CLP patients and normal controls (see FIG. 25a and 25b). While the source of the apo-E/spot 719 increase has not yet been identified, the present inventors believe its variation in individuals suffering CLP and CCP is important in the diagnosis and management of these conditions, as well as in peripheral nerve damage generally. It may also provide insight into the mechanism of neuronal regeneration.

Any number of protocols can be used to develop protein data for use in performing the diagnostic methods of the present invention. The protocol used in the present studies and as exemplified herein was approved by the IRB of St. Luke's Hospital in Houston, Tex., and patients and sex and age matched volunteers each of whom signed an informed consent letter. The patients were complaining of chronic (six months or more in duration) low back pain secondary to a reported injury and were randomly selected from one of the applicants' orthopedic practice. The patients were requested to remain drug-free for at least one week prior to blood sampling. The controls were free of significant medical problems as determined by medical history and physical examination. The initial study consisted of 10 patients and 10 sex and age matched controls. In the second study, a similar protocol consisted of 64 plasma samples from 36 lower back pain patients and 28 controls. The data for this study were obtained from three separate studies: two independent blinded studies, performed using the apo-E variant (spot 719) to determine which individuals had CLP, provided the correct diagnosis in sixteen out of seventeen patients (94.1%) and 14 out of 14 controls (100%); and a third study, which was not blinded, was performed and was accurate in 18 out of 19 patients (94.7%) and 14 out of 14 controls (100%).

Additional studies were undertaken which focused on spot 719.

These studies are set forth in the examples which follow.

To prevent degradation of samples of tissue, serum, or other body fluids (preferably blood and more preferably plasma) from the subjects, the sample is initially frozen in dry ice. At any point prior to electrophoresis a portion of the sample may be removed for counting and assaying the amount of protein by, for example, the Lowry method.

The first stage gels for the two-dimensional electrophoresis generally contain urea at a concentration of about 9M and about 2% nonionic detergent, both of which aid in dissociating proteins. The nonionic detergent helps keep the separated proteins from precipitating at their isoelectric points. These reagents and their proportions can vary somewhat, provided that these objectives are accomplished. An ampholyte (e.g., 2% 4–8 pH ampholyte) is also desirable to maintain a pH gradient across the length of the gel, although other reagents which maintain the pH gradient could be substituted. The acrylamide concentration of the first stage gel should be such as to permit protein movement to the isoelectric point. The first stage gel can be in a number of forms; for example, it can be housed in an isoelectric focusing tube or in a slab form. Preferably, the first dimension is in the form of a tube gel.

The samples are usually prepared for the first stage by solubilizing in either 10% sodium dodecyl sulfate (SDS) or urea at a concentration of about 9M. The reducing agent 2-mercaptoethanol is also usually included to separate disulfide-linked subunits. An ampholyte to maintain the pH gradient, a nonionic detergent which does not affect the protein charge, and dithiothrietol (DTT) which disrupts disulfide bonds, may also be included. Other reagents may also be added, or other reagents which accomplish the foregoing functions may be substituted. For example, prior to subjecting the samples to gel electrophoresis, the samples may be placed in a sample buffer (for example, 2% SDS, 2% DTT, 20% glycerol, 2% ampholines and 2% CHAPS) and placed in a boiling water bath (at about 100° C.) for about two minutes to aid in dissolution. This temperature and the time exposed thereto has been found to not cause protein degradation; however, both can be varied provided that dissolution takes place and protein degradation does not. The sample buffer unfolds the protein, separates the disulfide-linked subunits, and maintains the pH. Other sample buffers which accomplish the foregoing functions, and other methods of dissolving the protein samples, can also be used.

The samples may then be cooled on ice and treated with DNase and RNase to reduce the viscosity. The samples can then be snap-frozen in liquid nitrogen and packed on dry ice if they are not to be run on gels immediately. This adequately preserves the samples. However, it has been found that any method that cools a dissolved sample to −70° C. or more will also preserve the samples.

Polyacrylamide gel electrophoresis in the presence of SDS is usually used for the second dimension separation. SDS is an ionic detergent and binds strongly to proteins. It eliminates the native protein charge characteristics and unfolds the protein into a rod-like form. See Tracy et al., *J. Clin. Lab. Autom.*, supra. Thus, when protein is subjected to an electric field in the polyacrylamide gel matrix, the uniform negative charge and the relatively uniform shape of the SDS-protein complexes allow separation essentially by molecular weight, with the polyacrylamide gel matrix acting as a sieve.

The second stage gel is preferably SDS-equilibrated, to eliminate the protein charge, and contains a higher acrylamide concentration than the first stage gel, to aid in separating proteins by molecular weight. Other reagents can be added or substituted. Further, the second gel can be in a variety of forms; preferably, however, the second stage is in the form of a slab gel.

The spots on the gels can be viewed by any number of methods including staining with Coomassie blue and silver staining. They can be visualized for relative protein density manually, but it is preferred that they be scanned with an appropriate camera system with a normalization standard (available from the National Bureau of Standards, Gaithersburg, Md.) and analyzed with a computer densitometer to measure relative protein spot staining intensities or densities.

In order to perform immunological tests for the diagnosis and/or monitoring of CLP or CCP, the first step is to obtain antibodies to the proteins of interest. There are many methods of accomplishing this which are well known to those skilled in the art. (For comprehensive laboratory methods, see Harlow et al., *Antibodies: A Laboratory Manual*, Cold Spring Harbor Laboratory (1988), which is incorporated by reference herein.) For antibodies with sufficient specificity for western blots and immunoassays, the antigen must be purified to homogeneity or the antigen should be used to prepare monoclonal antibodies. Since the proteins of interest in this invention are seen as unique spots on the second dimension polyacrylamide gel, preferably the gel can be used as the final purification step of the individual antigens. One can obtain a pure antigen preparation by excising the spots which show increased or decreased intensity in CLP or CCP patients. This gel piece can be injected into an animal to raise antibodies. Alternatively, one may cut out the spot of protein and electroelute it from the gel to obtain a protein in solution for injection. Still another technique for processing the protein for injection after separation on gels is to electrophoretically transfer the proteins to nitrocellulose, locate the proteins of interest by staining (e.g., with Ponceau S), excise the spots and cut into pieces for injection. The particular method used is only limited by the ability to elicit an immune response to the proteins of interest.

As an alternative to using the antigen purified by separation on an electrophoretic gel directly, one may elute a protein spot, obtain a partial sequence by any method well known in the art, and use the sequence to manufacture synthetic peptides (usually with an automated machine using solid-phase techniques). The synthetic peptide should be at least six amino acids long to elicit antibodies that bind to the original protein. The purified synthetic peptides would then be coupled to carrier proteins, and these conjugates are then used to immunize animals.

The polyclonal antibodies in the antisera obtained with the foregoing methods can be used for western blots and other immunological tests. However, one may further utilize hybridoma technology to obtain monoclonal antibodies, which may be the best choice for immunochemical techniques. Methods of monoclonal production are well known in the art and were first described by Kohler and Milstein in 1975. Briefly, antibody-secreting cells are fused to, for example, myeloma cells to create hybridoma cells which are cloned and screened by appropriate methods for the desired antibodies. While a monoclonal antibody for apo-E is available (Chemicon), this antibody reacts not only with spot 719, but with the other apo-E spots cn the 2-D gel. In addition, the inventors' investigations showed that this commercially available monoclonal antibody does not demonstrate quantitative differences between CLP plasma and normal plasma. Therefore, it is an object of the present invention to obtain a monoclonal antibody specific for spot 719 to overcome the disadvantages with the currently available apo-E monoclonal. It is only spot 719, out of the complex of apo-E spots on the 2-D gel, which is increased in patients with peripheral nerve damage, in particular those patients suffering from CLP or CCP. The location of this spot on the 2-D gels suggests that it is a variant form of apo-E, which differs from the other apo-E proteins by its glycosylation or phosphorylation pattern or other novel post-translational event, or that it is associated with another protein or lipid which is not completely denatured prior to gel analysis.

One of the diagnostic methods of the present invention involves the detection of proteins which are present in patients with CLP or CCP, yet absent in normal controls. Besides locating these protein spots by staining on a two-dimensional gel, one may detect the proteins by immunoblotting, or western blotting, utilizing the polyclonal or monoclonal antibodies raised to the particular protein of interest. Protocols for immunoblotting are well known in the art and generally comprise the steps of gel electrophoresis, transfer, blocking, addition of antibody, and detection. The preparation of the sample and the two-dimensional gel electrophoresis is discussed above. At the completion of electrophoresis, proteins are transferred from the gel to a matrix, such as nitrocellulose, activated (diazo groups) paper and activated (positively charged) nylon. Nitrocellulose membranes are preferred for relatively low background and cost considerations; however, any membrane which will sufficiently bind the transferred proteins can be used. Preferably, transfer of thelproteins is accomplished by electrophoretic elution; however, simple diffusion or vacuum-assisted solvent flow can also be used. After transfer, the membranes may, optionally, be stained to determine the position of molecular weight markers.

Prior to antigen detection, one must block the membrane to prevent non-specific adsorption of immunological reagents. Most preferably, the blocking solution would be composed of nonfat dried milk or bovine serum albumin. After blocking, antigens can be detected directly or indirectly. Direct detection utilizes labelled primary antibodies. The antibodies, labelled with iodine, enzymes or biotin, can be prepared by methods well known to those skilled in the art. In indirect detection, the primary antibody (unlabelled) is first added to membrane, followed by a secondary antibody (an anti-primary antibody) which is labelled with radioactive iodine or an enzyme, such as horseradish peroxidase. The antigen is then detected by exposing a radiolabeled membrane to X-ray film or, in the case of enzyme-labelled antibody, by adding substrate to the membrane.

An alternative method of quantifying or detecting the presence of protein for the diagnosis of CLP or CCP is the use of immunoassays performed directly on the body fluid sample. Several immunoassays would be useful in the context of the present invention, including: antibody capture (Ab excess); antigen capture (antigen competition); and the two-antibody sandwich technique. All immunoassays rely on labeled antigens, antibodies, or secondary reagents for detection and quantitation. The label used can be radioactive, or enz,ymatic, or one may label with fluorochromes or biotin. The choice of label is a matter of discretion with the diagnostician, taking into consideration cost, sensitivity, radioactivity exposure, etc. The term "label" as used herein refers to any of the foregoing.

In an antibody capture type of assay, the test sample is allowed to bind directly to a solid phase and any unbound antigen is washed away. The antibody specific for the antigen is added and allowed to bind. The amount of antibody bound to the solid phase, after washing away unbound antibody, is determined using a secondary reagent. Suitable secondary reagents include anti-immunoglobulin antibody, protein A or protein G. These can be obtained from commercial sources or prepared by methods known in the art. Detailed protocols can be found in Harlow et al., supra, and are incorporated herein by reference, the particular methods used not being limited or essential to the practice of the present invention.

Antigen capture type assays measure the amount of antigen in a test sample via a competition between labeled and unlabeled antigen. This type of assay is exemplified by a "radioimmunoassay"or RIA. The first step in this type of assay is to bind unlabeled antibody to a solid support (either directly or through an intermediate protein, e.g., an anti-immunoglobulin antibody). A sample of known antigen of known quantity is labeled and a sample of this is added to the test material containing an unknown amount of antigen, and the mixture is added to the bound antibody. The antigen in the test sample competes with the labeled antigen for binding to the antibody bound to the solid support. Following removal of the unbound antigen, the amount of labeled bound antigen is measured. The higher the concentration of antigen in the unknown test sample is, the more effectively it competes with the labeled antigen; therefore, a decreasing amount of label is detected with an increasing amount of unlabeled antigen. Thus, generated standard titration curves will yield relative levels of antigen.

Another immunoassay to quantitate antigen concentration is the two-antibody sandwich technique. This type of assay requires two antibodies that bind to two separate epitopes of the antigen. Thus, one may use two monoclonals that recognize two separate sites on the antigen, or a batch of purified polyclonals can be used. The essential steps are as follows: 1) one purified antibody is bound to a solid phase and the antigen in the test sample is allowed to bind to the first antibody; 2) unbound antigen is washed away and a labeled second antibody is allowed to bind to the antigen; and 3) after washing, the second labeled antibody that is bound to the matrix is quantitated. As in other assays, a standard titration curve with known dilutions is plotted and the unknown sample is compared thereto. In order to determine absolute amounts, a standard curve generated with known quantities of antigen is used.

A wide variety of test kits are possible to take advantage of the advances in the diagnostic arts made possible by this invention. Some will be described here; others can be devised by those skilled in the art.

The central reaction in a test kit could be between any one of the aberrant proteins found in patients with peripheral nerve damage, in particular that which causes CLP and CCP and the antibodies prepared as set forth above and in the Examples below. The Examples below are directed to the preparation of antibody from rabbits, and the following description and other Examples of test kits and test methods will be based on the rabbit preparation. The rabbit is the preferred source of immunoglobulin and its fractions; however, the skilled artisan will recognize that the following Examples utilize the rabbit only as exemplary. Other animals can be used and this will require some modification of the other reagents used in the tests and the kits, and are readily apparent to one skilled in the art.

In the test kits, any of a variety of adsorbents can be used including, for example, glass or plastic surfaces which may be the inner surfaces of test tubes or the surfaces of test plates. Examples of flat surfaces especially useful in an enzyme-linked immunosorbant assay (ELISA) or a radio-immunoassay (RIA) include glass, nitrocellulose paper, or plastics such as polystyrene, polycarbonate or various polyvinyls. The ligands can be attached to the surface by direct adsorption, forced adsorption and coupling, in accordance with known procedures. Typical test kits are set forth in the Examples below.

The following Examples illustrate the utility of the diagnostic methods of the present invention, and are not intended to limit the scope of this invention. For instance, any of the known immunoassays or other known methods of protein detection may be used to aid in the diagnosis of peripheral nerve damage, in particular that nerve damage which causes CLP or CCP. Also, the method of diagnosis is not limited to the specific proteins elucidated by the present Examples. Modifications of the procedures as would be apparent to one skilled in the art are within the scope of the teachings.

EXAMPLE 1

In a first (initial) study, ten patients with chronic back pain were randomly selected from a group of patients complaining of CLP of six months or more secondary to a reported injury. These patients, 3 females and 7 males, ranged in age between 20 and 55 years. Of these patients, 7 were taking medication for their pain. However, 3 of these patients took no medication. The degree of lower back disability was evaluated by a number of factors such as: the history of the back pain (including radiations and the induction of pain with coughing and/or sneezing); physical examination including the loss of sensitivity in the L-4 to L-5 dermatomes; measurements of back and leg motion limitations; abnormalities in the knee jerk reflexes; and the analysis of spinal radiographies (for spondylosis, stenosis, herniated discs, degenerations, the narrowing of the intervertebral space, etc.)and other special studies such as MRI, CT scan, myelograms, discograms and electromyelograms. Controls were selected for age and sex to match the patient group. The controls were free of significant medical problems as determined by medical history and physical examination.

Ten ml of blood was collected by venipuncture, within one minute of tourniquet application, using Vacutainer tubes containing 143 USP units of heparin. The control samples were collected at the same time as those from the patients and all samples were collected during afternoon hours. Plasma was isolated by centrifugation of the whole blood at 2000×g for ten minutes followed by the separation of the plasma from the packed red and white cells by pipetting. The plasma was frozen at −20° C. prior to shipment (in dry ice) to the laboratory for analysis. The samples were stored at −70° C. until electrophoresis, which was performed within three months of venipuncture.

Gel electrophoresis. Plasma samples were thawed and 20 ul of each sample were added to 20 ul of denaturing solution, containing 10% w/v SDS and 2.3% DTT w/v. The samples were then heated to 95° C. for 4 minutes followed by cooling to room temperature. Then 96 ul of electrophoresis solution, containing 0.1 g DTT, 0.4 g CHAPS, 5.4 g urea, 0.5 ml pH 3.5–10 ampholytes and 6.5 ml deionized water were added to each sample. The samples were mixed on a Vortex mixer and 10 ul of each processed sample (containing 1.47 ul plasma) were added to the first dimension isoelectric focusing (IEF) gels. Isoelectric focusing was performed in 3% (w/v) acrylamide gels with 4% w/v ampholytes (containing a 1:1 mixture of pH 3.5–10 and pH 5–7 ampholytes) and crosslinked with 0.03% diacryloylpiperazine, i.e., 3% T/1% C. Electrophoresis was performed for 18,000 volt hours, beginning with 1000 volts for 17 hours followed by 2000 volts for 30 minutes.

The second dimension, wherein proteins are separated by mass, was performed with 160 cm×200 cm×1.5 mm slab gels using a Bio-Rad Protean II chamber. These gels were formed with 12.2% acrylamide (w/v), 0.2M TRIS-HCl (pH 8.8), 0.7% sodium thiosulfate (w/v), 0.3% diacryloylpiperazine (w/v), 0.5% 1,4-dimethylpiperazine(v/v), and 0.07% ammonium persulfate (w/v). Electrophoresis was performed at 7° C. with a constant current of 40 mA per gel until a dye front reached at or near the bottom of the gel.

Silver staining. At the end of the run, the gels were removed from the glass plates and washed for 5 minutes in water (no protein loss is detected during this period). The gels were then soaked in a solution of ethanol/acetic acid/deionized water (40/10/50) for one hour on an orbital shaker at 36 rpm. This solution was then replaced with a solution of ethanol/acetic acid/deionized water (5/5/90) and the gels were soaked for at least 3 hours. The gels were washed with deionized water for 5 minutes and soaked in 10% gluteraldehyde solution for 30 minutes. Extensive washes with deionized water were performed to entirely remove the gluteraldehyde 3×10 and 4×30 minutes). [Cold deionized water (<15° C.) removes gluteraldehyde more efficiently.] the gels were then stained for 10 minutes in an ammoniacal silver nitrate solution (6 g of silver nitrate dissolved in 30 ml of deionized water), which is slowly mixed into a solution containing 160 ml of water, 10 ml of concentrated ammonium hydroxide, and 1.5 ml of sodium hydroxide, 10 mol/liter; this solution is then diluted with deionized water to a final volume of 750 ml) (solution H). The temperature of solution H was 20° C. After staining, the gels were washed with deionized water for 5 minutes×3. The image was then developed in a citric acid and formaldehyde solution (0.1 g citric acid and 1 ml formaldehyde in 1 liter of deionized water) (solution V) until a slight background stain appeared. (The optimum temperature of solution V is 15°–18° C.) The development process was stopped with an acetic acid /deionized water solution (5/95) for at least 15 minutes. Stained gels were stored in a glycerol/ethanol/ deionized water solution (7/10/83). [This staining method is described in Hochstrasser et al., Analytical Biochemistry, 173, pp. 424–435 (1988).]

Gel analysis. In order to quantitate proteins, gels were scanned with an Eikonics Series 78/99 digital scanner and the gel images created thus were analyzed using PDQUEST software (Protein Database, Inc., Huntington Station, N.Y.) on a SUN 4-260 minicomputer. Gel images were normalized for protein loading and staining variation using the average log-ratio normalization procedure of the PDQUEST software. Thirteen hundred proteins were analyzed on each gel and the proteins were matched and compared quantitatively. This analysis was performed by using the PDQUEST software aided by visual examination and operator intervention in gel areas containing complex spot patterns. All proteins which increased or decreased in concentration by three-fold or more, and were found to be statistically significant (by way of the Student t test or the log Student t test) were considered to be spots of interest.

Figure 2:
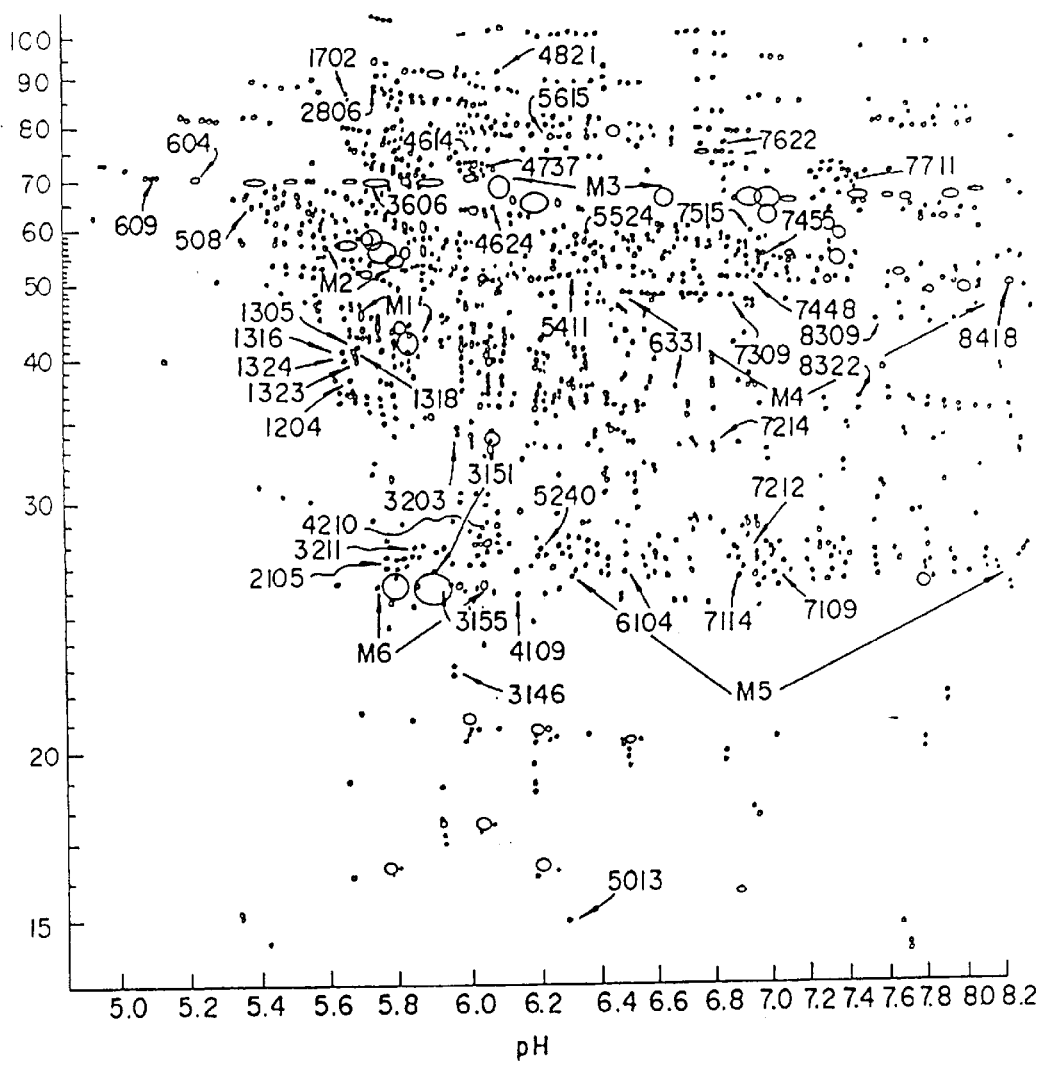
FIG. 2: A computer generated diagram of all the proteins analyzed in the initial study. The numbered proteins are the same as those identified in FIG. 1.
Figure 3C:
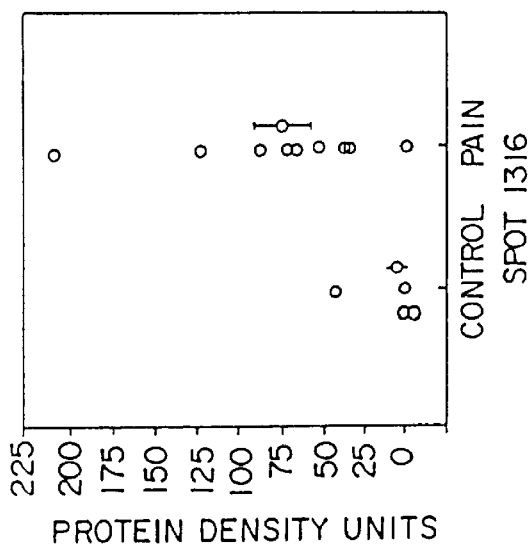
FIG. 3: A scatter diagram illustrating proteins which showed robust correlations with CLP in the initial study. The numbers to the left of the circles indicate the frequency greater than 1 that a patient with that value was observed. The circle and bar to the right of each group of data indicate the mean and the standard error of the mean for that group.
Figure 3B:
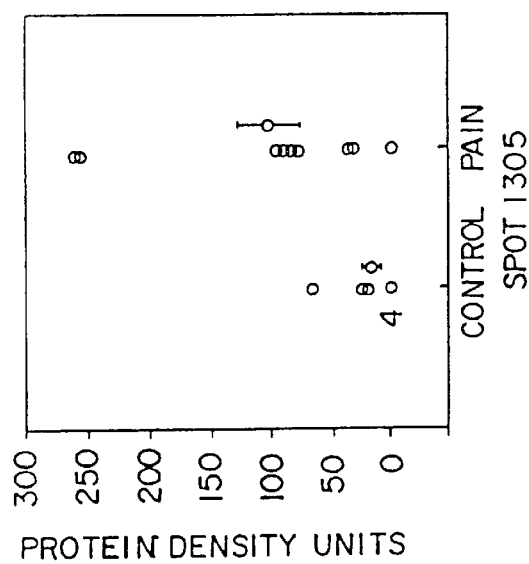
Figure 3A:
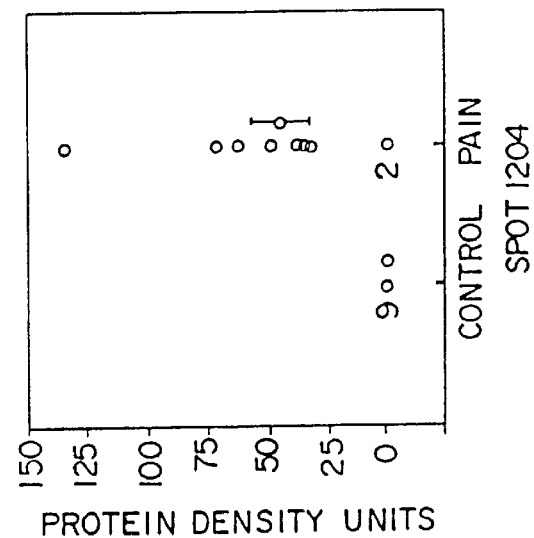

FIG. 1 represents a stained gel of a plasma sample from a control subject. Marker proteins are designated by the prefix M, and Table I lists the marker plasma proteins landmarked on the gel. Proteins which were found to be increased or decreased in patients with CLP are listed in Tables II and III, respectively, and are indicated by number on the gel shown in FIG. 1. Those proteins which are absent in patients' plasma are illustrated by open circles on the control gel in FIG. 1. A computer-generated master map of the proteins analyzed in this Example is represented in FIG. 2.

TABLE I

Landmarked Plasma Proteins

| Identification No. | Protein |
|---|---|
| M1 | beta-Haptoglobins |
| M2 | alpha$_1$-Antitrypsins |
| M3 | Albumin |
| M4 | IgG heavy chains |

TABLE I-continued

Landmarked Plasma Proteins

| Identification No. | Protein |
|---|---|
| M5 | IgG light chains |
| M6 | Apo A-1 lipoproteins |

TABLE II

Plasma Proteins Increased With CLP

| Pro-tein ID # | Controls (N = 9) | | | Patients (N = 10) | | | Fold Increase or Decrease |
|---|---|---|---|---|---|---|---|
| | Mean Conc.* | S.E.M. | Fre-quency | Mean Conc.* | S.E.M. | Fre-quency | |
| 4210 | 0.0 | 0.0 | 0 | 51.5 | 24.2 | 5 | >51.5 |
| 1204 | 0.0 | 0.0 | 0 | 46.5 | 12.3 | 8 | >44.5 |
| 1318 | 0.0 | 0.0 | 0 | 42.5 | 15.3 | 7 | >42.5 |
| 1324 | 0.0 | 0.0 | 0 | 38.3 | 14.7 | 6 | >38.3 |
| 1702 | 0.0 | 0.0 | 0 | 31.2 | 13.9 | 4 | >31.2 |
| 4821 | 0.0 | 0.0 | 0 | 31.2 | 16.6 | 4 | >31.2 |
| 0508 | 0.0 | 0.0 | 0 | 26.4 | 9.2 | 5 | >26.4 |
| 3211 | 0.0 | 0.0 | 0 | 25.5 | 9.7 | 5 | >25.5 |
| 4109 | 0.0 | 0.0 | 0 | 21.9 | 10.1 | 4 | >21.9 |
| 5524 | 0.0 | 0.0 | 0 | 20.2 | 10.5 | 4 | >20.2 |
| 7622 | 0.0 | 0.0 | 0 | 19.8 | 8.2 | 4 | >19.8 |
| 6331 | 0.0 | 0.0 | 0 | 13.0 | 5.4 | 4 | >13.0 |
| 8322 | 0.0 | 0.0 | 0 | 10.1 | 4.5 | 4 | >10.1 |
| 3151 | 1.6 | 1.6 | 1 | 46.8 | 15.2 | 7 | 29.3 |
| 1323 | 2.0 | 2.0 | 1 | 50.0 | 18.2 | 6 | 25.0 |
| 5240 | 3.4 | 3.4 | 1 | 69.2 | 30.7 | 6 | 20.3 |
| 2105 | 2.0 | 2.0 | 1 | 31.5 | 11.8 | 6 | 15.8 |
| 1316 | 4.9 | 4.9 | 1 | 75.2 | 18.1 | 9 | 15.3 |
| 6104 | 7.4 | 4.7 | 2 | 94.5 | 41.2 | 6 | 12.8 |
| 7109 | 18.5 | 12.3 | 3 | 131.2 | 42.9 | 6 | 7.1 |
| 3606 | 63.7 | 30.5 | 4 | 402.8 | 130.0 | 8 | 6.3 |
| 1305 | 17.3 | 7.4 | 5 | 103.8 | 28.0 | 9 | 6.0 |
| 3146 | 3.7 | 3.7 | 1 | 21.0 | 4.8 | 7 | 5.7 |
| 7114 | 23.3 | 15.5 | 2 | 118.2 | 38.5 | 7 | 5.1 |
| 7448 | 67.7 | 46.3 | 3 | 283.4 | 79.4 | 9 | 4.2 |
| 3203 | 4.2 | 4.2 | 1 | 17.5 | 8.2 | 6 | 4.2 |
| 0609 | 37.3 | 19.1 | 3 | 148.3 | 46.5 | 8 | 4.0 |
| 0604 | 62.9 | 29.0 | 4 | 236.0 | 61.5 | 9 | 3.8 |
| 7711 | 15.4 | 15.4 | 1 | 49.4 | 17.3 | 6 | 3.2 |
| 5615 | 89.1 | 89.1 | 1 | 226.8 | 64.9 | 8 | 2.5 |

*Concentrations are in arbitrary density units.
p is less than or equal to 0.05

TABLE III

Plasma Proteins Decreased With CLP

| Pro-tein ID # | Controls (N = 9) | | | Patients (N = 10) | | | Fold Increase or Decrease |
|---|---|---|---|---|---|---|---|
| | Mean Conc.* | S.E.M. | Fre-quency | Mean Conc.* | S.E.M. | Fre-quency | |
| 4737 | 224.0 | 152.1 | 5 | 0.0 | 0.0 | 0 | >224.0 |
| 4624 | 112.5 | 52.0 | 4 | 0.0 | 0.0 | 0 | >112.5 |
| 7212 | 78.1 | 28.1 | 6 | 0.0 | 0.0 | 0 | >78.1 |
| 7309 | 13.0 | 5.8 | 4 | 0.0 | 0.0 | 0 | >13.0 |
| 7214 | 11.7 | 6.0 | 3 | 0.0 | 0.0 | 0 | >11.7 |
| 2806 | 11.6 | 4.7 | 4 | 0.0 | 0.0 | 0 | >11.6 |
| 5013 | 10.8 | 5.6 | 3 | 0.0 | 0.0 | 0 | >10.8 |
| 4614 | 12.5 | 4.4 | 6 | 2.3 | 1.6 | 2 | 5.4 |
| 3155 | 76.0 | 28.5 | 7 | 16.5 | 9.1 | 4 | 4.6 |
| 8309 | 53.8 | 11.0 | 9 | 13.1 | 4.7 | 5 | 4.1 |
| 8418 | 744.1 | 185.6 | 8 | 191.1 | 108.6 | 5 | 3.9 |
| 7455 | 95.6 | 26.8 | 7 | 25.5 | 10.9 | 4 | 3.7 |
| 5411 | 79.4 | 23.4 | 7 | 25.7 | 13.2 | 3 | 3.1 |
| 7515 | 8.2 | 2.6 | 6 | 3.2 | 1.9 | 3 | 2.6 |

*Concentrations are in arbitrary density units.
p is less than or equal to 0.05

EXAMPLE 2

In a further, expanded study ("second study"), 36 patients with chronic low back pain (two cases having lumbar and thoracic pain—cases 14 and 32) and controls, were subjected to the methods set forth in Example 1. This protocol was approved by the Institutional Review Board of St. Luke's Hospital in Houston, Tex. All CLP patients (n=36), selected from one of the present inventors' (BMC) clinical practice, all normal volunteers (n=28), and all patients with conditions other than CLP (n=34) (see further Example 3) signed an approved consent form and were requested, prior to blood sampling, to remain drug-free for at least one week. The CLP patients were diagnosed by clinically correlating the information obtained from their medical history, physical examination, x-ray examination, selected imaging techniques (MRI and/or CT scanning) and invasive techniques when indicated (myelograms and/or discograms). Healthy controls were questioned regarding and CLP symptoms and were eliminated if they had any history of CLP. Patients with the other conditions (see further Example 3) were diagnosed using standard history and physical examinations and the indicated laboratory, x-ray and imaging techniques.

Venapuncture from the anticubital fossa was performed and each 5 mls. of blood was collected into a Vacutainer tube containing 143 USP units of sodium heparin. It was centrifuged at 783×G for ten minutes at room temperature and the plasma was removed and placed into a plastic tube and frozen at −20° C. These samples were shipped overnight to the electrophoresis facility and remained frozen at −70° C. until used. The plasma samples were subjected to 2-D gel electrophoresis and staining as in Example 1.

In an effort to identify new spots, the patient gels were compared to control gels visually without the aid of computer analysis, as well as also using the computer analysis. It was observed that one particular protein(s) spot appeared in patients and was virtually absent in controls. It is postulated that the computer did not identify this spot because it was incorporating it into another, very closely located spot on the gel. This new spot has been designated 1bp13–14.719 (or spot 719). Its presence is indicated on FIGS. 12–14 and 18–20, and the corresponding absence of the spot on the control gels is indicated by an open circle in FIGS. 15–17 and 21–23.

A summary of the data obtained in this study is shown in Tables IV and V. In gels where spot 719 was barely or not visible, they were scored as negative (−). In gels which clearly contained the spot, they were scored as positive (+). The data in Table V were obtained from three separate studies: two independent blinded studies and a third non-blinded study. The studies were "blind" to the extent that the investigator performing the analyses was unaware which gels were of back pain samples and which were controls. As can be seen from Tables IV and V , the accuracy in predicting which samples belonged to which group is remarkably high (97.22% overall). Moreover, this new spot allows for visual identification without the need for computer-assisted analysis, thereby simplifying the diagnostic procedure. In order to quantify the increase in spot 719, a portion of the gels were subjected to computer-assisted analysis using the ELSIE software (developed by Mark Miller and Arthur Olson at the National Cancer Institute, USA), the results of which are shown in FIGS. 25a and b.

TABLE IV

Back Pain Study of Example 2

| Pt. | Age | Sex | WC | Atty | Surg | 719 | Diagnosis | Med |
|---|---|---|---|---|---|---|---|---|
| 1. | 31 | M | + | + | 1 | + | HNP L5-S1. | 0 |
| 2. | 35 | M | + | 0 | 1 | + | HNP L4-5, L5-S1; Scar. | 0 |
| 3. | 47 | F | 0 | 0 | 1 | + | Spondylosis, HNP L4-5. | 0 |
| 4. | 56 | F | 0 | 0 | 1 | + | Pseudoarthrosis L4-5. | T13;R |
| 5. | 44 | M | + | + | 2 | − | Donor Site Pain. | 0 |
| 6. | 43 | M | + | + | 5 | + | Psuedoarthosis L4-S1; Stenosis L3-4, L4-5; Scar | 0 |
| 7. | 24 | M | + | + | 0 | + | HNP L4-5, L5-S1. | T13 |
| 8. | 49 | M | 0 | 0 | 2 | + | Stenosis L2-8; Psuedo-arthrosis, L4-5. | VIC |
| 9. | 43 | M | + | + | 5 | + | Deg. Spondylolisthesis L3-4; Psuedoarth. L4-S1. | 0 |
| 10. | 37 | M | + | + | 1 | + | HNP, Spondyiosis, Stenosis, L4-5. | 0 |
| 11. | 47 | M | 0 | 0 | 1 | + | HNP L4-5, L5-S1. | 0 |
| 12. | 26 | M | + | + | 2 | + | Spondylolythesis L5-S1; Pseudo-arthrosis L5-S1. | 0 |
| 13. | 30 | M | + | + | 2 | + | Recurrent HNP L4-5. | 0 |
| 14. | 60 | F | 0 | 0 | 0 | + | Osteoporosis, Osteoarthritis. | 0 |
| 15. | 50 | F | 0 | 0 | 0 | + | Deg. Spondylolisthesis L4-5; DDD. L4-5; L5-S1. | 0 |
| 16. | 63 | M | + | 0 | 0 | + | HNP L4-5; L5-S1. | 0 |
| 17. | 44 | M | + | 0 | 4 | + | DDD, HNP, Psuedoarthrosis L4-5. | 0 |
| 18. | 48 | M | + | + | 2 | + | DDD, HNP, Spondyiosis, Pseudo-arthrosis, L4-5. | 0 |
| 19. | 26 | F | + | 0 | 0 | + | HNP L5-S1; DDD L4-5. | 0 |
| 20. | 42 | F | + | + | 2 | + | Lumbar Stenosis; Pseudo-arthrosis, L4-5. | 0 |
| 21. | 49 | M | + | + | 5 | + | HNP L5-S1; Arachnoiditis. | 0 |
| 22. | 27 | F | + | 0 | 0 | + | HNP L4-5. | 0 |
| 23. | 34 | M | + | + | 0 | + | HNP L4-5. | 0 |
| 24. | 44 | M | 0 | 0 | 1 | + | HNP L4-5. | 0 |
| 25. | 44 | F | + | + | 1 | + | HNP L4-5. | VIC |
| 26. | 26 | M | + | + | 0 | − | Spondylosis | 0 |
| 27. | 52 | F | + | 0 | 3 | + | L5-S1. DDD, Spondylosis L3-4; HNP L4-5. | 0 |
| 28. | 48 | M | + | + | 1 | + | HNP L3-4; Buldge L4-5. | 0 |
| 29. | 29 | M | + | + | 3 | + | Lumbar Stenosis L4-S1; Sacralization L-5 | 0 |
| 30. | 38 | F | + | + | 2 | + | HNP L4-5, L5-S1; DDD L4-5; Stenosis L5-S1. | NAP. ROB. |
| 31. | 52 | M | + | 0 | 2 | + | HNP, Spondylosis L4-5. | 0 |
| 32. | 59 | F | 0 | 0 | 0 | + | Scoliosis; Spondylosis. | 0 |
| 33. | 31 | M | + | + | 6 | + | HNP L5-S1; Facet damage L5; Arachnoiditis. | 0 |
| 34. | 42 | M | + | + | 3 | + | HNP, Instability L3-4; Stenosis L4-5. | 0 |
| 35. | 31 | M | + | + | 2 | + | HNP, facet damage L5-S1. | 50 |
| 36. | 34 | M | + | + | 1 | + | Spondy-lolisthesis L5-S1. | 0 |

Table IV. Clinical data from 36 CLP patients in a study which included 23 controls: WC=workman's compensation case; Atty=attorney involvement; Surg=number of back operations at the time of venapuncture; 719=increased (+) or decrease (−) in the plasma level of the apolipoprotein E variant scored as described in Methods; HNP=herniated nucleus pulposis; DDD=degenerative disc disease; Med= drugs; NAP=Naprosyn; ROB=Robaxin; VIC.=Vicodin; T#3=Tylenol#3.

TABLE V

Back Pain Study of Example 2

| Subjects | CLP Patients | Controls | Patients and Controls |
|---|---|---|---|
| Apo E increase | 34+  2− | 0+  28− | 62/64 |
| Correlation | 34/36 | 28/28 | 62/64 |
| Test | Sensitivity | Specificity | Efficiency |
| Percentage | 94.44% | 100.00% | 97.22% |

Table V. Statistical analysis of CLP data: Results of the plasma studies of 36 CLP patients and 28 normal controls. The efficiency was calculated as = (sensitivity + specificity)/2.

EXAMPLE 3

Five additional groups of patients' plasma were analyzed with respect to 1bp13–14.719. These groups consisted of:

A. Three patients who were relieved of their CLP through surgery and two unoperated, asymptomatic individuals who had biomechanical abnormalities that often produced chronic lower back pain. None of these patients displayed an increase in the apolipoprotein E variant (spot 719) associated with chronic lower back pain (see Table VI).

B. In order to determine the significance of the location of the pain in the spinal column in inducing the presence of the apolipoprotein E variant from patients with CLP, plasma samples were analyzed from four individuals with chronic cervical pain (CCP). All four patients with CCP demonstrated the apolipoprotein E variant (spot 719) (see Table VII).

C. To determine if normal nociception without nerve damage induced an increase in the apolipoprotein E variant (spot 719), the plasma proteins of 11 patients with painful orthopedic injuries without nerve damage were analyzed. Only one of these patients, who may have sustained nerve damage, displayed an increase in the apolipoprotein E variant (see Table VIII).

D. Nerve damage is thought to be associated with CLP. To determine whether other peripheral nerve damage causes the induction of apolipoprotein E variant (spot 719) and plasma, which is associated with CLP, the plasma samples of six individuals with various peripheral nerve problems were examined. Five of the six displayed an increase in the apolipoprotein E variant. The remaining patient had a painless radial nerve palsy. (See Table IX).

E. Local inflammatory responses (which often include edema and demyelination) of the nerve root have been demonstrated with chronic lower back pain. To determine if the increase in apolipoprotein E (spot 719) was associated with known inflammatory conditions, the plasma of seven patients with chronic systemic inflammatory changes (lupus erythematosus, rheumatoid arthritis, and Crohn's disease) was studied. Three patients with Crohn's disease and two with lupus displayed an increase in the apolipoprotein E variant (spot 719), while the two with rheumatoid arthritis did not. (See Table X).

The above samples were subjected to the methods and analyses of Example 2, wherein the presence or absence of 1bp13–14.719 was determined.

These studies were undertaken to answer the questions previously posed in this specification. In particular, (1) is pain required or is only a biomechanical change required to increase the plasma level of the apolipoprotein E variant? In Group A, five asymptomatic patients with biomechanical changes were tested: two with spondylolisthesis, two with post-operative discectomies, and one with a post-operative discectomy and fusion. None exhibited an increase in the apolipoprotein E variant. This study indicated the association of the protein (spot 719) with pain, and also strongly suggested that the protein difference was not due to painless surgical scarring (see Table VI).

(2) Is the induction of the apolipoprotein E variant (spot 719) from the spine limited only to chronic pain in the lumbar region? To determine if the increase in the plasma level of apolipoprotein E variant is specific for pain in the lumbar region, we examined the plasma of four patients with CCP (Group B). All four demonstrated a significant increase in this protein. This study indicated that pain associated with nerve damage anywhere in the spinal column may be associated with increased plasma concentrations of this protein.

(3) Is the apolipoprotein E variant increased in all patients with acute or chronic pain? For this study, the area of nociception was extended to the periphery and 11 patients were selected with various painful conditions without nerve damage (Group C). These conditions ranged from a fractured ulna to a ligamentous shoulder injury. Ten were negative for an increase (90.9%) and one was positive for an increase in the apolipoprotein E variant (see Table VIII). This one patient had a multitude of serious orthopedic injuries (with probable nerve damage), and it could not be determined which of them was responsible for the positive result. This study suggested that peripheral pain without nerve damage does not produce the protein (spot 719).

(4) Is an increase in the plasma apolipoprotein E variant found in patients with painful conditions associated with peripheral nerve damage? An increase in this protein was found in individuals with chronic pain associated with the vertebral column, but was not found in individuals with peripheral pain who did not have evidence of nerve damage. This suggested that the protein variant found in the plasma of chronic spinal column pain patients was associated with chronic nerve damage, but was not associated with normal nociception with no nerve damage. On the other hand, it was postulated that peripheral pain due to nerve damage would be associated with an increase in the plasma level of the apolipoprotein E variant (spot 719). To test this hypothesis, the plasma from six patients with peripheral nerve damage (Group D) was tested. (See Table IX). Five of six were positive for an increase in the plasma concentration of the apolipoprotein E variant. The patient with an adventitious bursa was later diagnosed with cervical spondylosis and operated with relief of her symptoms. The one patient who displayed no increase in this protein had a painless radial nerve palsy. Since apolipoprotein E is known to be associated with nerve regeneration, it is possible that there was no physiological stimulus to repair the nerve. The incidence of spontaneous regeneration of the radial nerve following fractures of the humerus has been reported variously to be 70–92% with neuropraxia or axonotomesis, but 0% with neuronotomesis. The absence of an increase in the plasma level of apolipoprotein E variant and the absence of regeneration correlated with the clinical picture. From this study and those above, it is reasonable to suggest that nerve damage and regeneration are necessary to produce an increase in the plasma level of the apolipoprotein E variant (spot 719). Thus, the absence, or substantial absence, of spot 719 in a patient diagnosed by conventional methods to have peripheral nerve damage (for example, a radial nerve palsy), would indicate that there has been a lack of nerve regeneration. This would guide the clinician to treat the patient with therapy known to stimulate nerve regeneration. This would be especially helpful to a clinician watching the clinical course of a brachial plexus injury, a radial nerve palsy, a peroneal palsy, a peripheral neuropathy, a causalgia, etc.

(5) Is an increase in plasma apolipoprotein E variant (spot 719) related to inflammation? In addition to stimulating regeneration, nerve damage has been noted to stimulate a local, neural inflammatory response. It is possible that mediators of inflammation are necessary for nerve regeneration, because apolipoprotein E is known to be involved in both responses. To answer this, a group of patients with diseases known to stimulate chronic inflammation (Crohn's disease, lupus erythematosus and rheumatoid arthritis) was studied (Group E). Three patients with Crohn's disease and two with lupus were positive; but the two with rheumatoid arthritis were negative (see Table X). From this study, it is possible to conclude that the increase in the plasma concentration of this apolipoprotein E variant may be associated with chronic inflammatory diseases, which can produce false positives with respect to the diagnosis of peripheral nerve damage, and in particular, CLP and CCP.

It is known in the literature from biochemical studies of crushed sciatic nerves in rats, rabbits and primates that apolipoprotein E was essential for nerve repair in mammals, and that its local concentration may be increased 250-fold.

There is evidence that apolipoprotein E enters the nerve to a limited degree from the plasma, but it is produced in massive quantities by the resident macrophages and endothelial cells within the nerve, as well as monocyte-derived macrophages which enter the nerve in response to denervation. It is thought that apolipoprotein E may be involved in the redistribution of lipid (involving macrophages and Schwann cells), including the cholesterol released during degeneration to the regenerating axons. Apolipoprotein D, apolipoprotein A-I and AIV are also thought to be associated with this lipid transfer. Although these other apolipoproteins have been observed in the present studies, it is significant to note that these proteins do not appear to be useful as diagnostic markers of peripheral nerve damage. For instance, apo-D is reported in the literature to be locally increased (around the nerve tissue) 500-fold, but a corresponding increase in the plasma is not seen (see FIGS. 25a and b). The experimental data and human data in the prior art indicate that nerve pressure or tension can produce intraneural vascular changes, which ultimately result in degeneration which stimulates regeneration. It was postulated in the prior art that these perturbations produced a loss of nerve function and/or hyperexcitability with pain from ectopic generation. The increase in apolipoprotein E, which has been observed in animal nerve injury studies, is consistent with the increased plasma levels with apolipoprotein E variant observed in the plasma of patients with nerve injury in this study. This protein alteration may be part of a normal physiological response to nerve damage, and its presence can serve as a useful marker in the disorders associated with nerve damage, in particular in the diagnosis and management of patients with CLP and CCP.

TABLE VI

GROUP A

| Patient | Age | Sex | Diagnosis | Spot 719 |
|---|---|---|---|---|
| 1 | 67 | M | Spondylolisthesis L4-5 | — |
| 2 | 45 | M | Spondylolisthesis L5-S1 | – |
| 3 | 49 | M | Lam., Disectomy, HNP L5-S1 | – |
| 4 | 59 | M | Lam., Disectomy, Fusion, L5-S1 | – |
| 5 | 44 | M | Lam., Disectomy, L5-S1 | – |

TABLE VII

GROUP B

| Patient | Age | Sex | Diagnosis | Spot 719 |
|---|---|---|---|---|
| 1 | 35 | F | Cervical Spondylosis | + |
| 2 | 39 | F | Cervical Spondylosis | + |
| 3 | 38 | F | Cerv. Spondy.; Lam., fusion C5-6 | + |
| 4 | 41 | M | Cervical Spondy.; Detach. Deltoid. | + |

TABLE VIII

GROUP C

| Patient | Age | Sex | Diagnosis | Spot 719 |
|---|---|---|---|---|
| 1 | 68 | F | Lumbar Spondylosis; THR. | – |
| 2 | 59 | M | Failed THR. | – |
| 3 | 22 | M | Early Aseptic Necrosis, hip. | – |
| 4 | 34 | M | Ligamentous Tear, Shoulder | – |
| 5 | 15 | M | Right Knee MCL Sprain | – |
| 6 | 34 | M | Asep. Nec. L Hi,p; Discl. SC Jt. | – |
| 7 | 47 | F | Shoulder Pain. | – |
| 8 | 34 | F | Fractured Right Ulna, | – |
| 9 | 40 | M | Asept. Necrosis, Bilat. Hips | – |
| 10 | 29 | F | Knee Pain: Synovitis, tear MM. | – |
| 11 | 58 | M | Failed THR; Multi. Comp. Fracts. | + |

TABLE IX

GROUP D

| Patient | Age | Sex | Diagnosis | Spot 719 |
|---|---|---|---|---|
| 1 | 24 | M | Radial nerve palsy; frct. humerus | – |
| 2 | 42 | F | Cubital Tunnel Syndrome | + |
| 3 | 47 | M | Morton's Neuroma | + |
| 4 | 33 | M | Reflex Sympathetic Dystrophy | + |
| 5 | 47 | M | Left knee; Failed fixator | + |
| 6 | 46 | F | Adventitious Bursa, Left scapula | + |

TABLE X

GROUP E

| Patient | Age | Sex | Diagnosis | Spot 719 |
|---|---|---|---|---|
| 1 | 12 | F | Crohn's Disease | + |
| 2 | 27 | F | Crohn's Disease | + |
| 3 | 36 | F | Crohn's Disease | + |
| 4 | 33 | F | Crohn's Disease | + |
| 5 | 33 | F | Lupus. | + |
| 6 | 60 | F | Rheumatoid Arthritis. | – |
| 7 | 76 | M | Rheumatoid Arthritis. | – |

EXAMPLE 4

Immunoblot analysis was conducted for spot 719. Proteins separated by one and two dimensional gel electrophoresis electroblotted on PVDF membranes (Immobilon-P, Millipore), prepared according to the manufacturer's instructions, for 40 minutes at 0.8 amps using a transblot (BioRad) semi-dry electroblotter. The blots were then dried and placed in methanol followed by blocking overnight with PBS containing bovine serum albumin. ECL (Amersham) detection was performed according to the manufacturer's instructions using 1:1000 dilution of monoclonal anti-apo-E (Chemicon) for two hours at room temperature and 1:25000 antimouse immunoglobulin (Pierce) for 30 minutes. Spot 719 was positive for anti-apo-E reactivity (FIG. 26). Other modified forms of Apo-E were also detected. These latter spot densities were analyzed by computer-assisted densitometry for quantitative variations correlating with chronic lower back pain, and there were none (FIGS. 25a and 25b).

EXAMPLE 5

Amino acid N-terminal microsequence of amido black-stained electroblotted protein was performed. Automated peptide microsequencing was performed by dansyl-Edman degradation as described by B. S. Hartley (1970), Strategy and Tactics in Protein Chemistry, Biochem. J., Vol. 119, pp. 805–822, with modifications described by John M. Walker (1984) Proteins, Vol. 1, The Humana Press, pp. 221–242. In order to determine the preparative ability of the 2-D gel, the maximum plasma protein capacity for resolving spots 719 was determined by titering the sample load. It was determined that the optimal load for 2 D resolution and visualization with amido black of spot 719 was 60 microliters of sample (three times the analytical load). Spot 719 was excised from five amido black-stained preparative 2-D gel electroblots. N-terminal microsequence analysis was performed on spot 719 and was determined to be apo-E (FIG. 27). N-terminal sequence analysis determined 100% homology with the known sequence for apo-E.

EXAMPLE 6

To determine whether there is a correlation between protein spot density and the severity of pain, the densities of the various proteins of interest in the initial study were compared to the degree of lower back disability, as scored by historical as well as physical and radiological determinations.

A short, abbreviated scoring system (abbreviated from a scale of 144 possible factors) was devised which is similar to the Waddell approach [Waddell and Main, "Assessment of severity in lowback disorders", Spine, Vol. 9, pp. 204–208 (1984); Waddell, Main, Morris, Paola and Gray, 1984; Waddell et al, 1980]. The physical signs which Waddell et al selected as being significant were: degree of lumbar flexion; straight leg raising; root compression signs; and previous lumbar surgeries. The six clinical signs used in the abbreviated scale were similar and constituted the clinical objective scale (COS):

1. Scar from previous back surgery. All back surgery creates permanent scarring with permanent changes, no matter how subtle. This contributes to the presence of minute to major back pain. Each surgery scored 2.

2. True spasm which the patient cannot control (the most significant sign of all). This is not a limitation of motion which the patient can control, but true, uncontrolled spasm which the physician can recognize. Although sometimes painless in a condition such as burned out ankylosing spondylitis, it otherwise invariably signals severe pain. The physician can easily recognize this exception. This finding scored 4.

3. Straight leg raising (SLR) (right and left). This must be differentiated from hamstring spasm and a functional SLR. Hamstring spasm or tightness produces pain locally in the thigh, not in the back with SLR. Functional SLR is easily recognized by having the patient sit on the edge of the table and casually extend the knee. If the patient does not complain of back pain, there is no positive SLR. In knowledgeable hands, this is an objective finding. Each SLR scored 2.

4. Knee or ankle reflex change (right and left). These are objective findings in all cases. It is possible for them to be present without pain because of old trauma or surgery. Some reflex changes are associated with weakness or atrophy, but because these findings are frequently not recorded, it is not practical to score the latter. Each reflex change scored 1.

Table XI summarizes the COS.

TABLE XI

Summary of COS

| FACTOR | VALUE |
| --- | --- |
| Each back incision (scar) | 2 |
| Spasm | 4 |
| Right Straight Leg Raising (RSLR) | 2 |
| Left Straight Leg Raising (LSLR) | 2 |
| Right Reflex Change (RRC) | 1 |
| Left Reflex Change (LRC) | 1 |

The abbreviated scoring of the patients of this study are seen in Table XII, below. The numbers indicted next to the gel are arbitrarily assigned patient numbers.

TABLE XII

Scores of COS of Patients.

| Patient | SCAR | SPASM | RSLR | LSLR | RRC | LRC | TOTAL |
| --- | --- | --- | --- | --- | --- | --- | --- |
| gel 1 | 2 | 4 |  | 2 |  |  | 8 |
| gel 3 |  |  |  | 2 |  |  | 2 |
| gel 5 |  |  |  |  |  |  | 0 |
| gel 7 | 2 |  | 2 |  |  |  | 4 |
| gel 9 |  |  |  |  |  |  | 0 |
| gel 11 |  |  | 2 | 2 | 1 |  | 5 |
| gel 13 | 2 |  |  | 2 |  |  | 4 |
| gel 15 | 2 | 4 | 2 | 2 |  | 1 | 11 |
| gel 17 |  |  |  |  |  |  | 0 |
| gel 19 | 2 |  |  | 2 |  | 1 | 5 |

Figure 5:
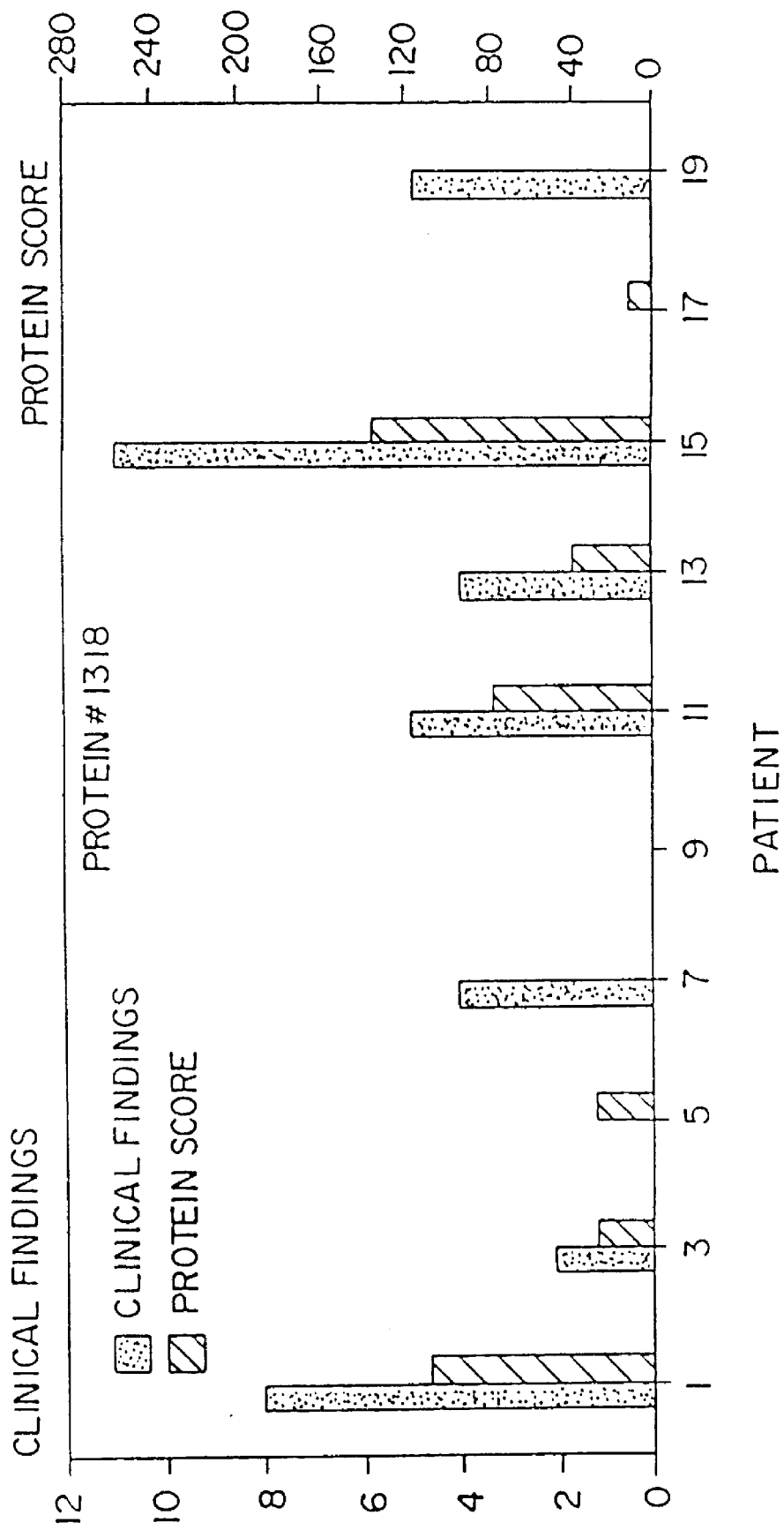
FIG. 5: A patient by patient comparison of protein 1318 densities with the degree of lower back disability. The degree of disability was scored by using a number of factors, such as: measurements of back and leg motion limitations, abnormalities in the knee jerk reflexes and history of back surgery.
Figure 6:
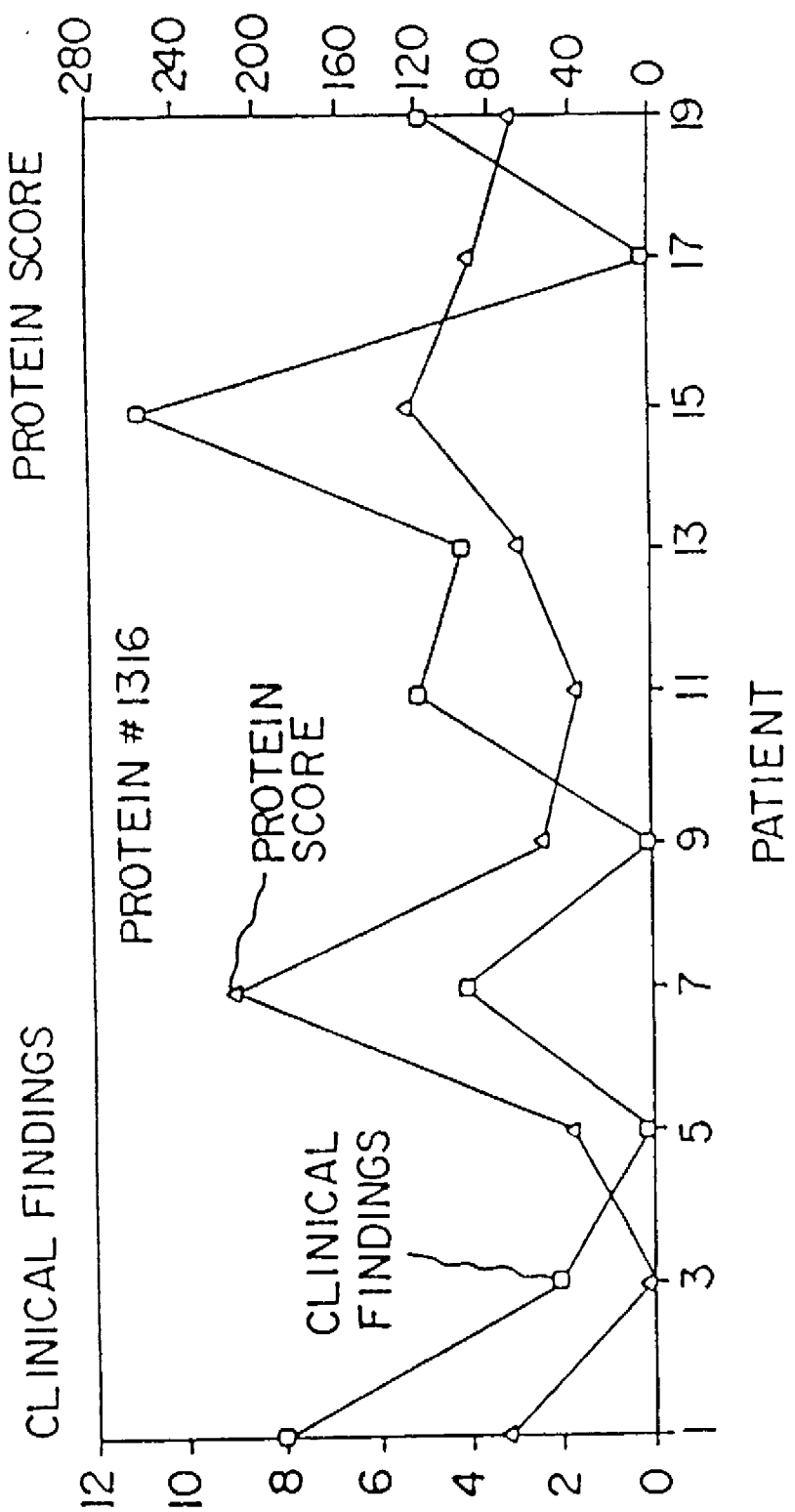
FIG. 6: A patient by patient comparison of protein 1316 densities with the degree of lower back disability.
Figure 7:
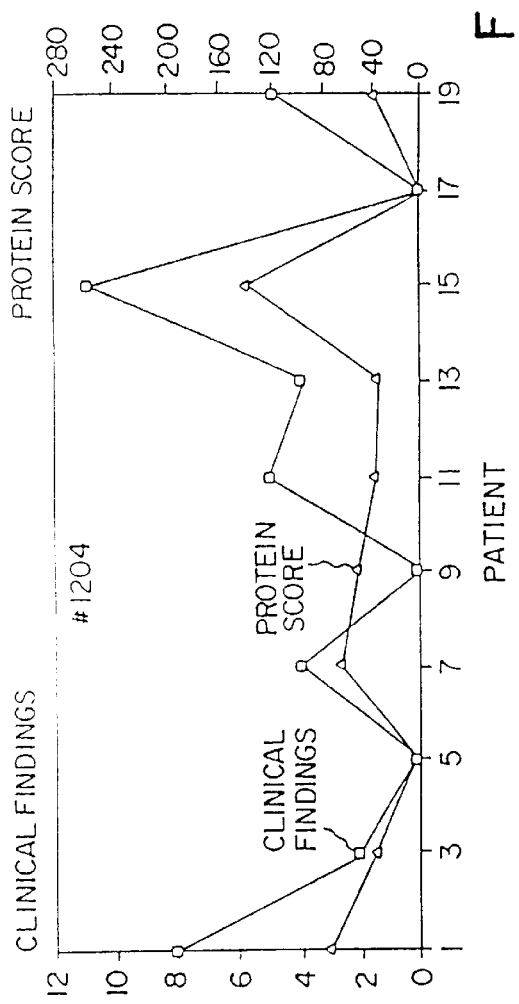
FIG. 7: A patient by patient comparison of protein 1204 densities with the degree of lower back disability.
Figure 8:
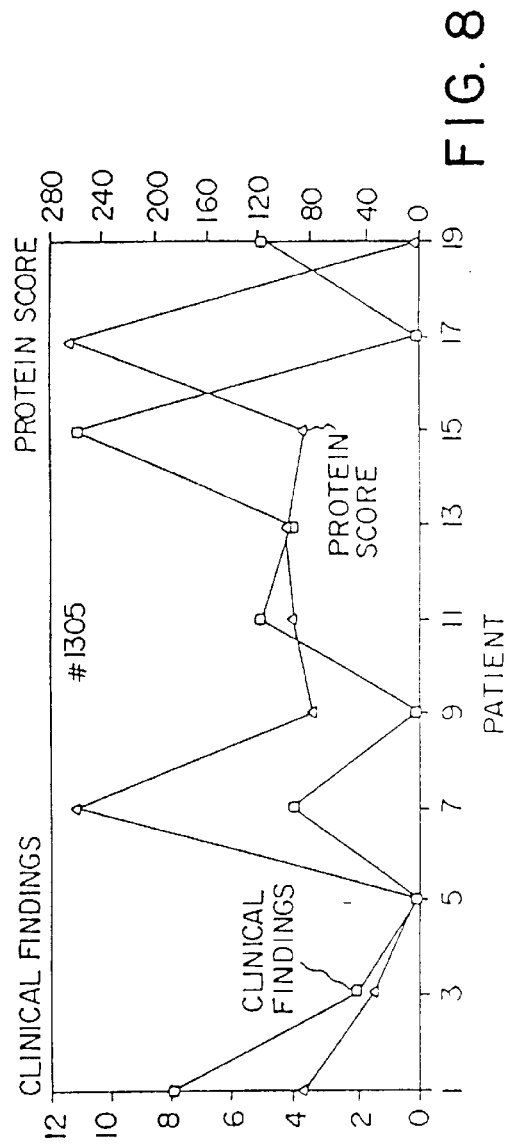
FIG. 8: A patient by patient comparison of protein 1305 densities with the degree of lower back disability.
Figure 9:
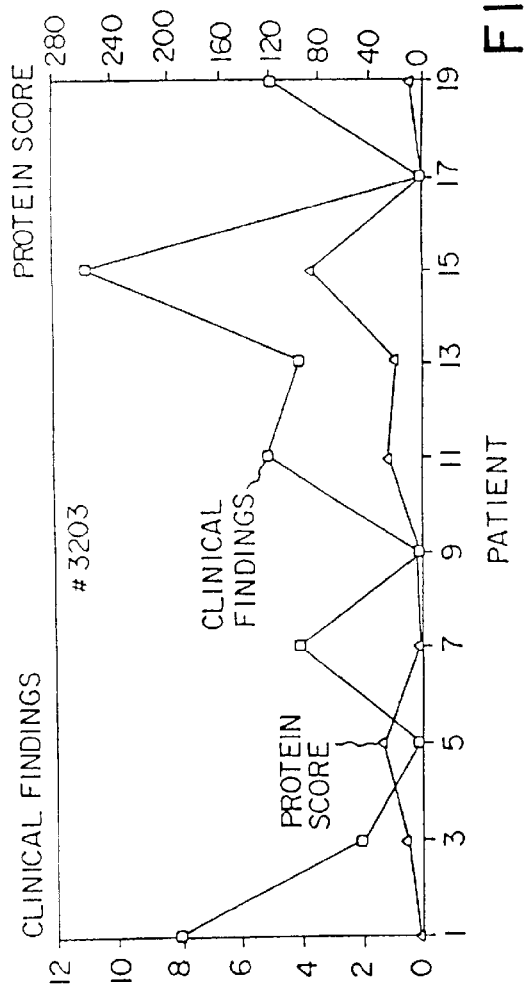
FIG. 9: A patient by patient comparison of protein 3203 densities with the degree of lower back disability.
Figure 10:
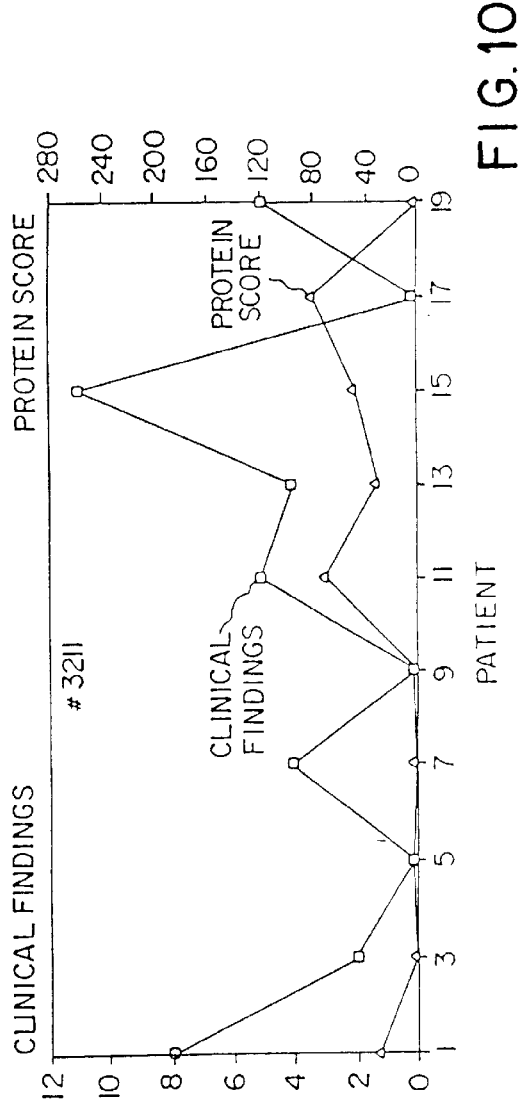
FIG. 10: A patient by patient comparison of protein 3211 densities with the degree of lower back disability.
Figure 11:
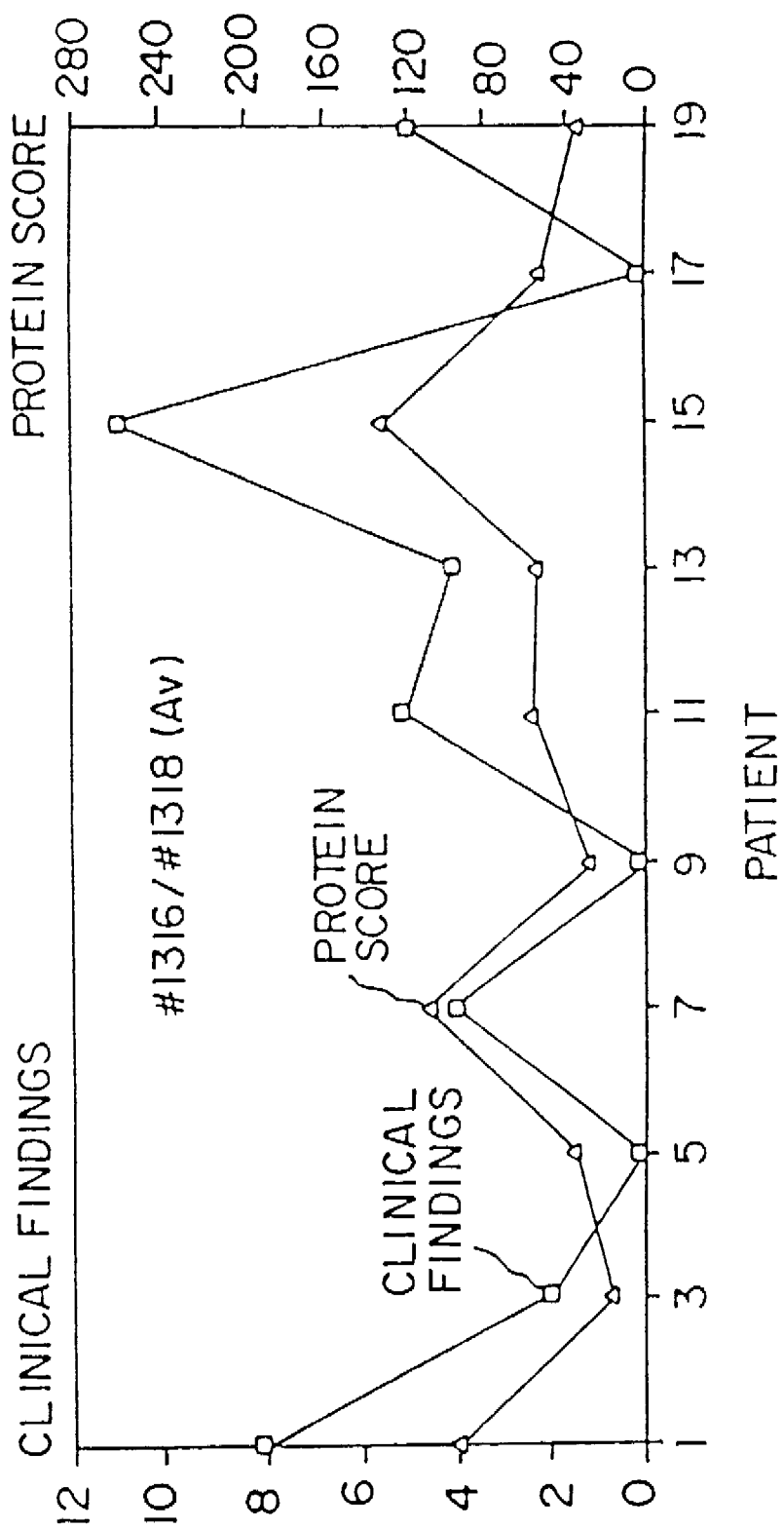
FIG. 11: A patient by patient comparison of the average of proteins 1316 and 1318 densities with the degree of lower back disability.
Figure 12:
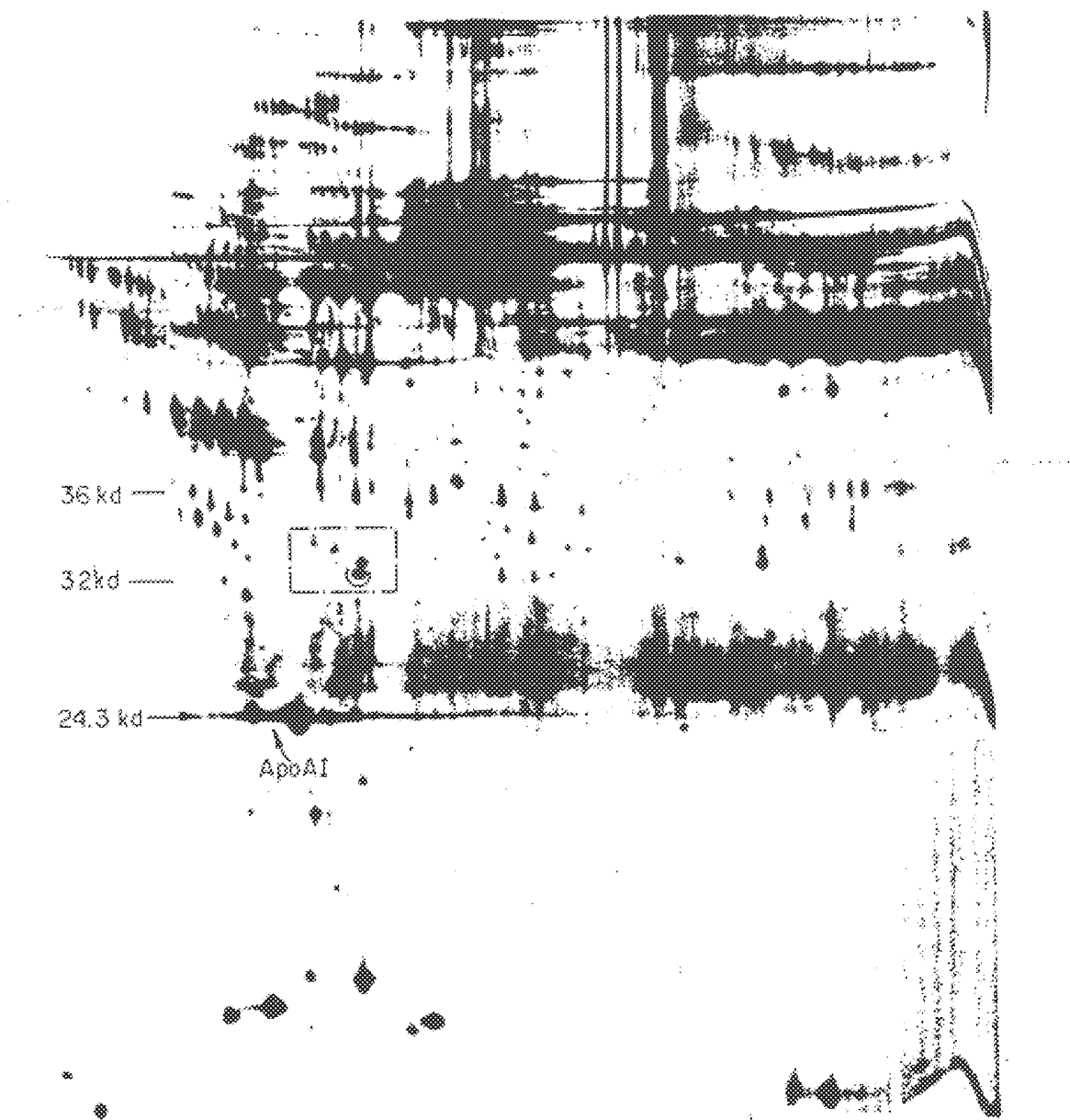
FIGS. 12–14: 2-D gel images of three patients with chronic lower pain back in the second study, showing the spot 1bp13–14.719.
Figure 13:
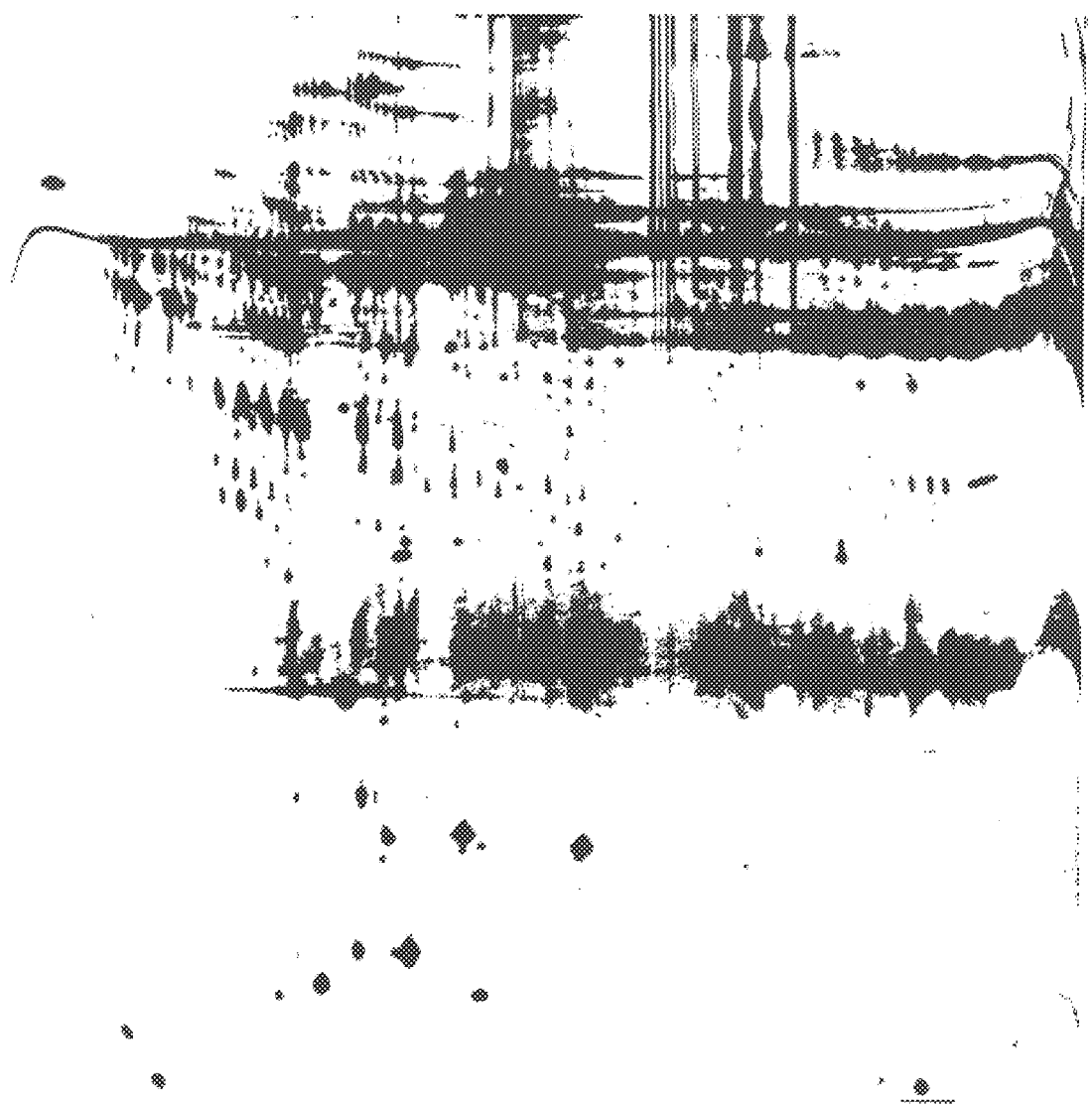
Figure 14:
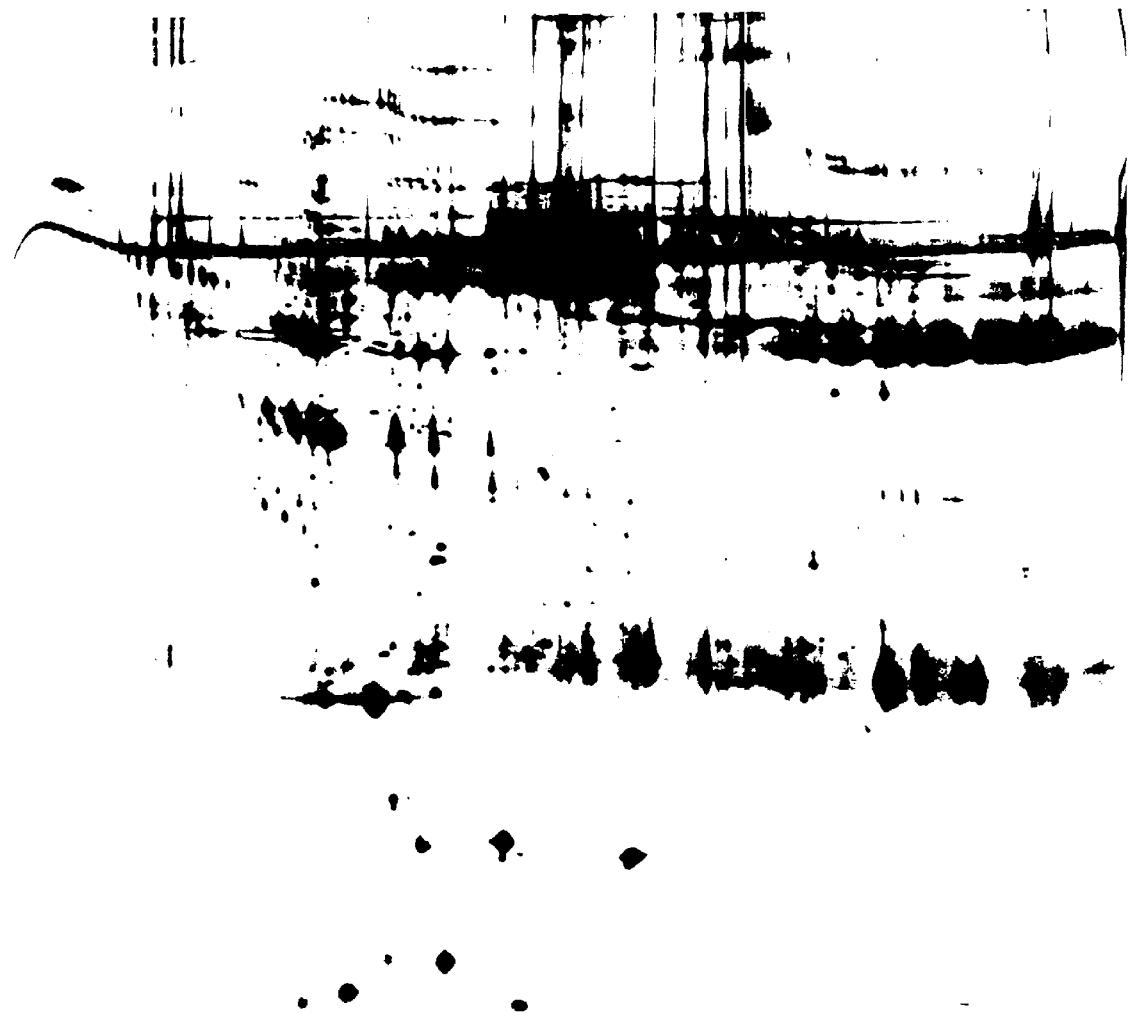
Figure 15:
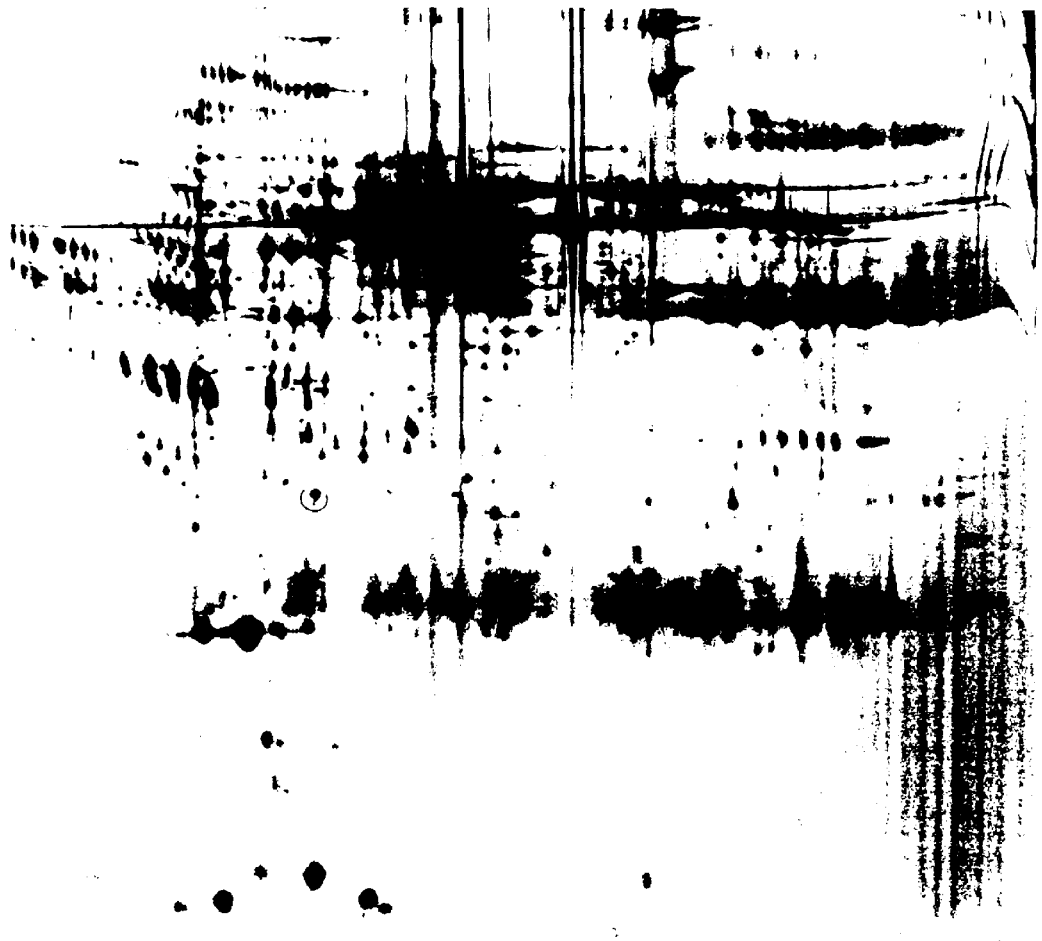
FIGS. 15–17: 2-D gel images of three controls run side-by-side with the gels of FIGS. 12–14. Open circles represent area where 1bp13–14.719 spot is missing.
Figure 16:
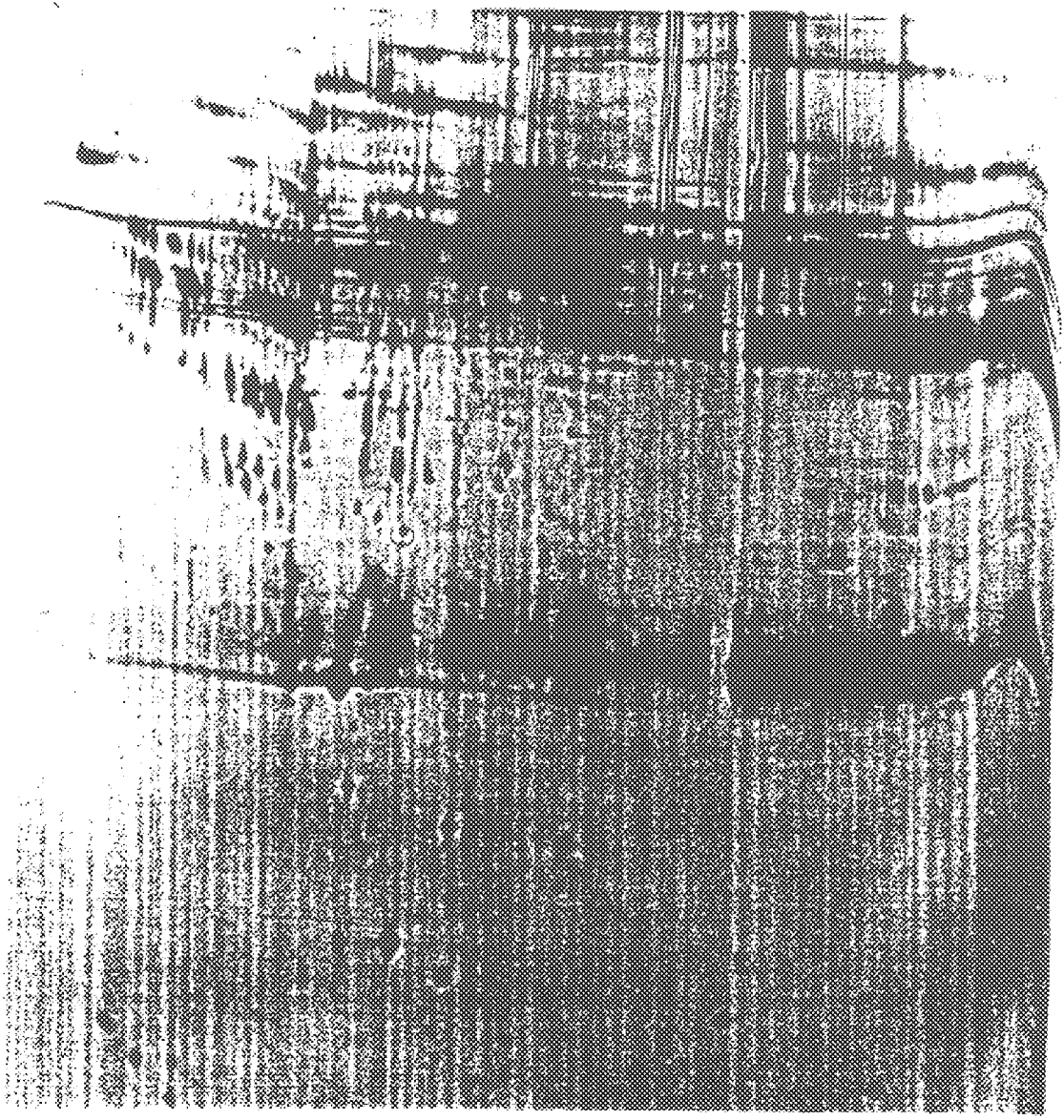
Figure 17:
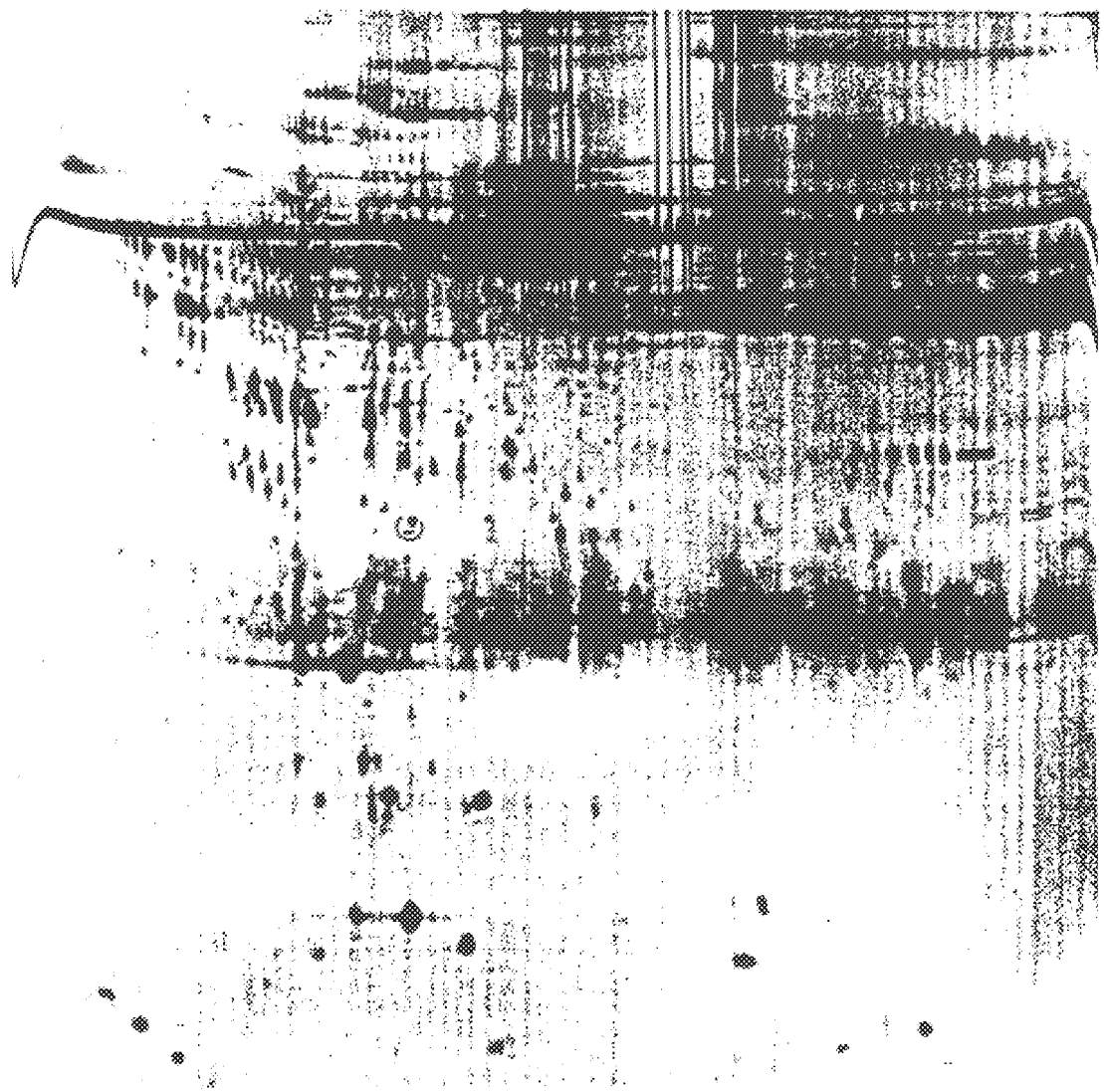
Figure 18:
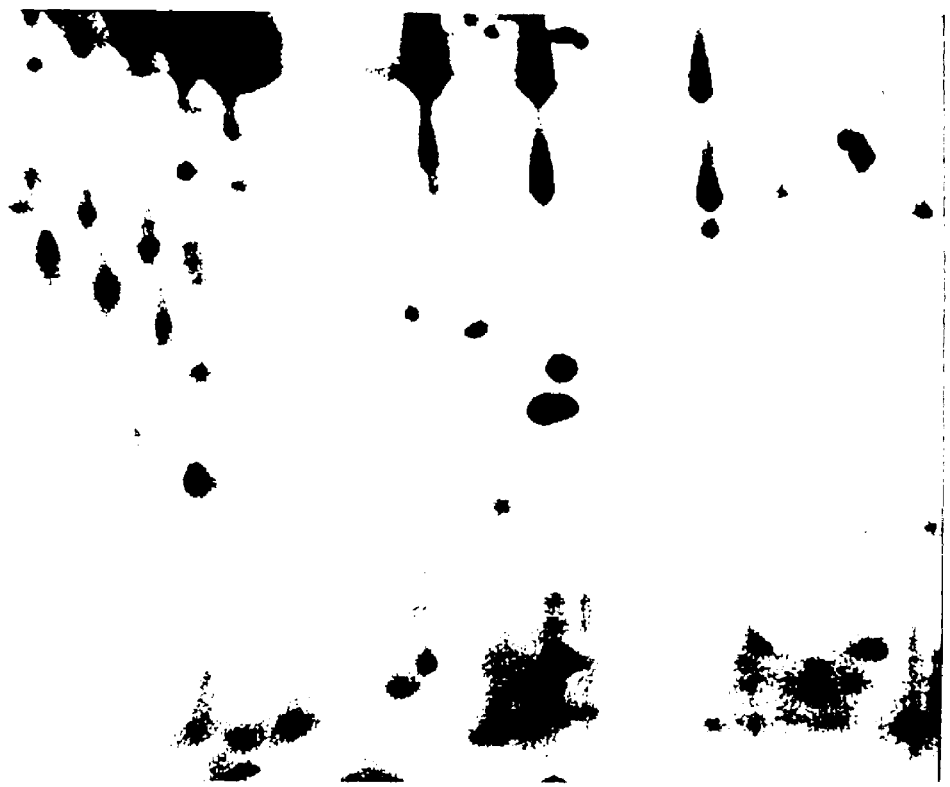
FIGS. 18–20: Represent enlargements of the areas blocked off in FIGS. 12–14.
Figure 19:
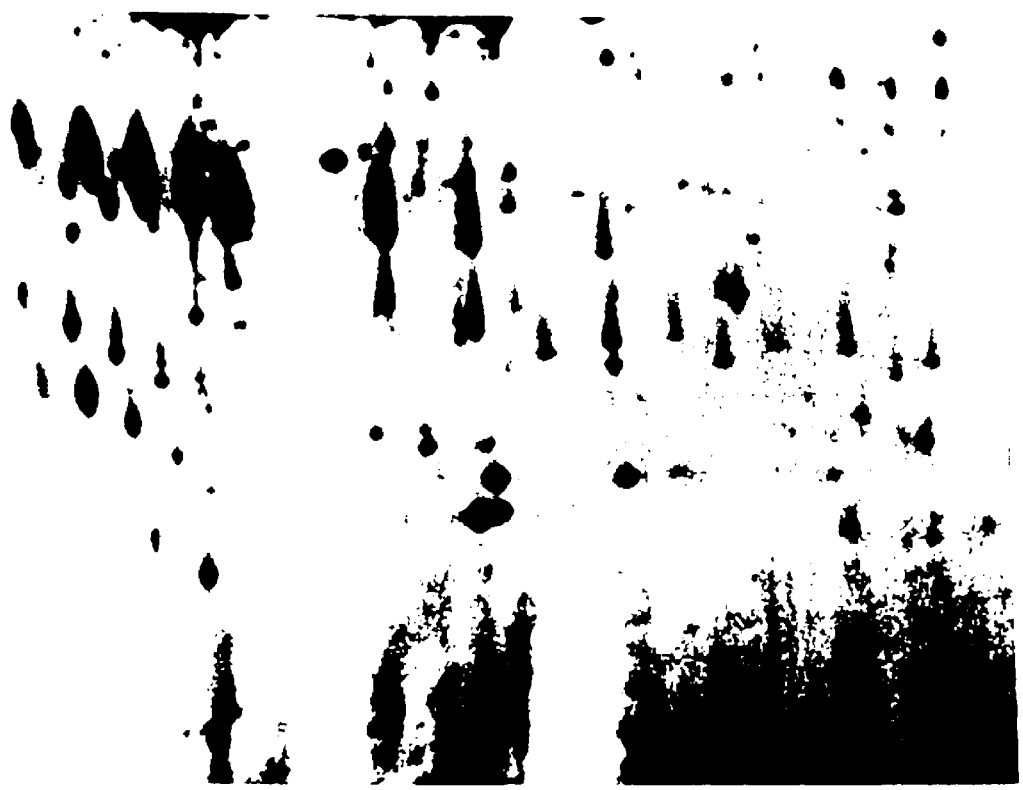
Figure 20:
Figure 21:
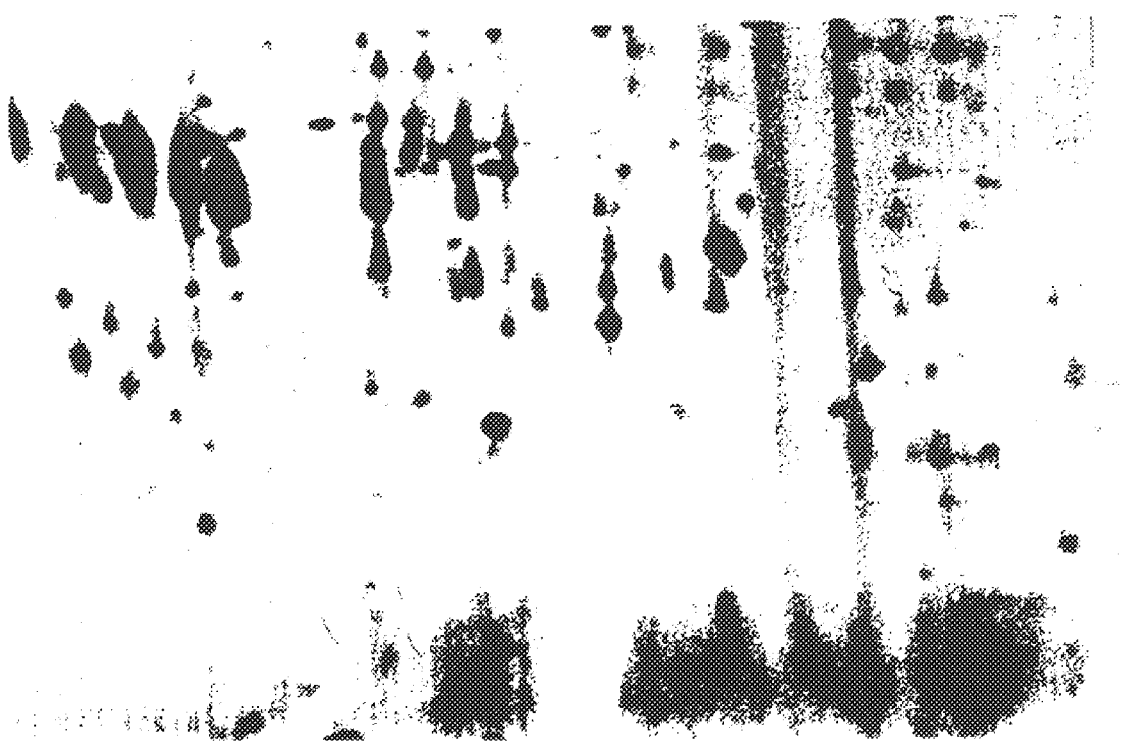
FIGS. 21–23: Represent enlargements of the areas blocked off in FIGS. 15–17.
Figure 22:
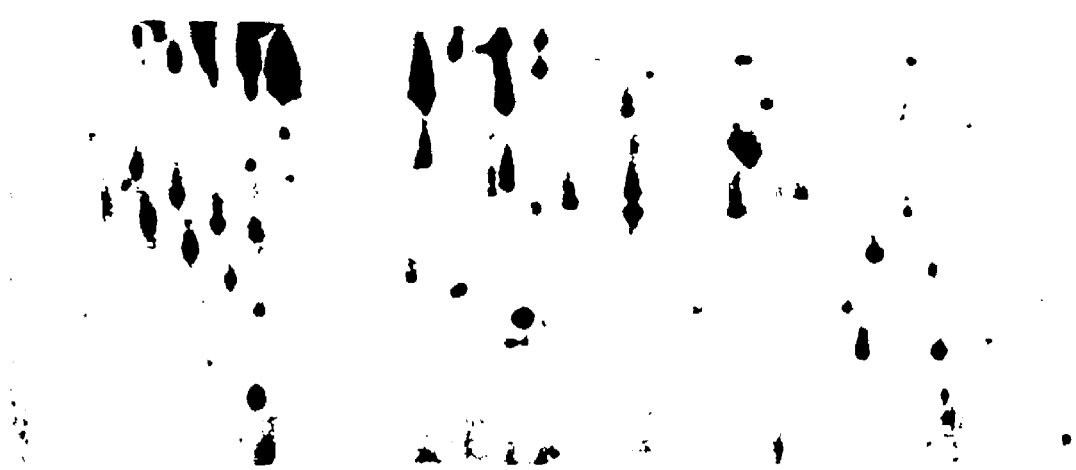
Figure 23:
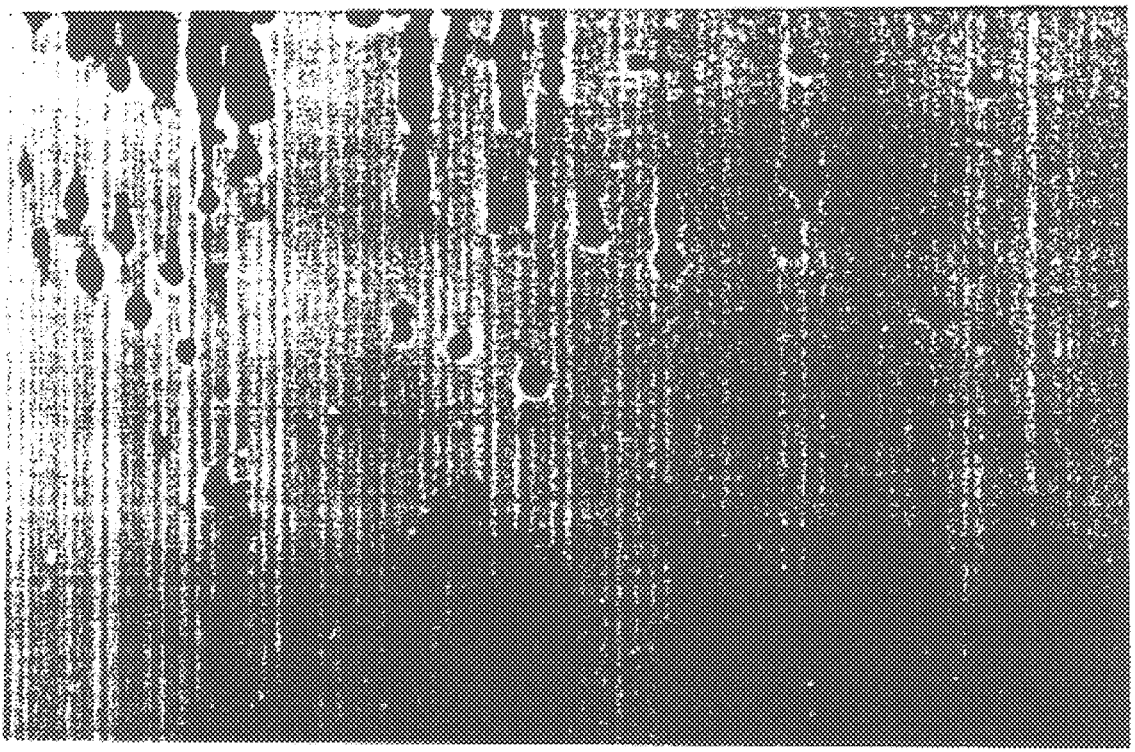
Figure 24A:
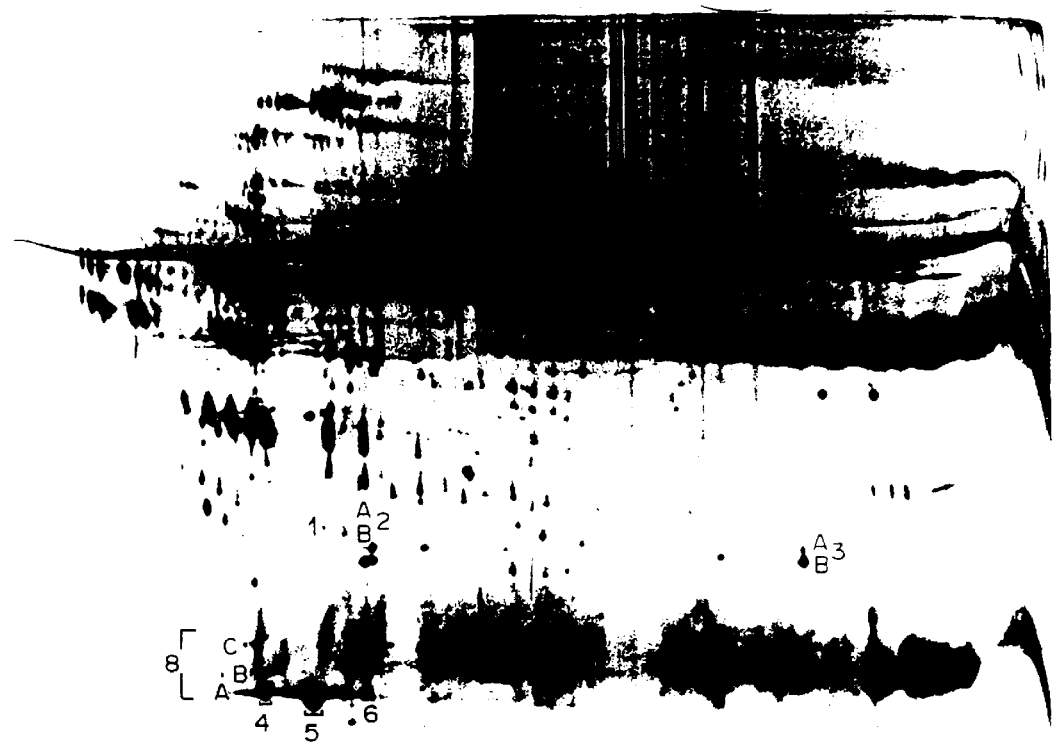
FIGS. 24a–c: These are photographs of 2-D gels of the present invention.
Figure 24B:
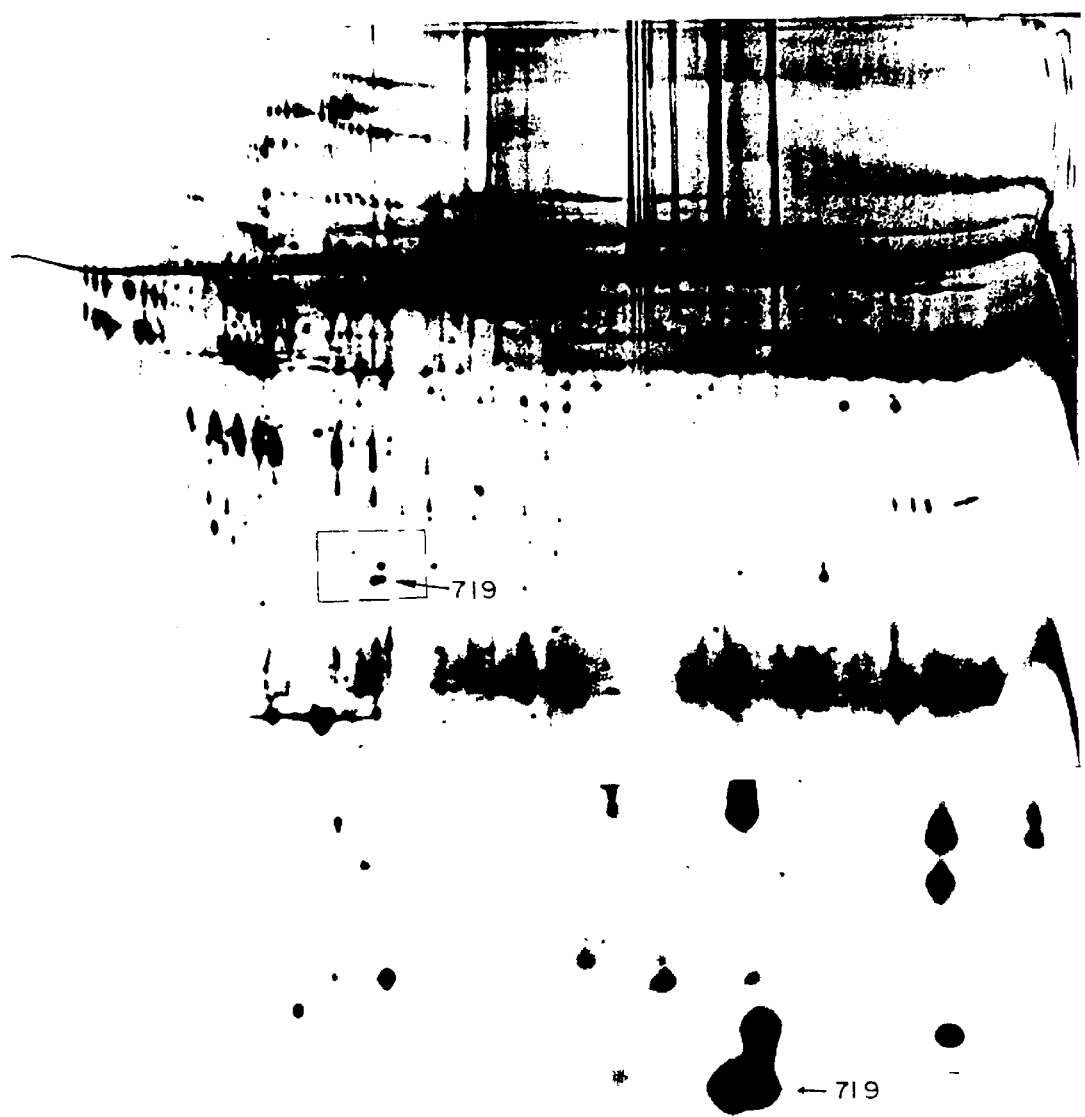
Figure 24C:
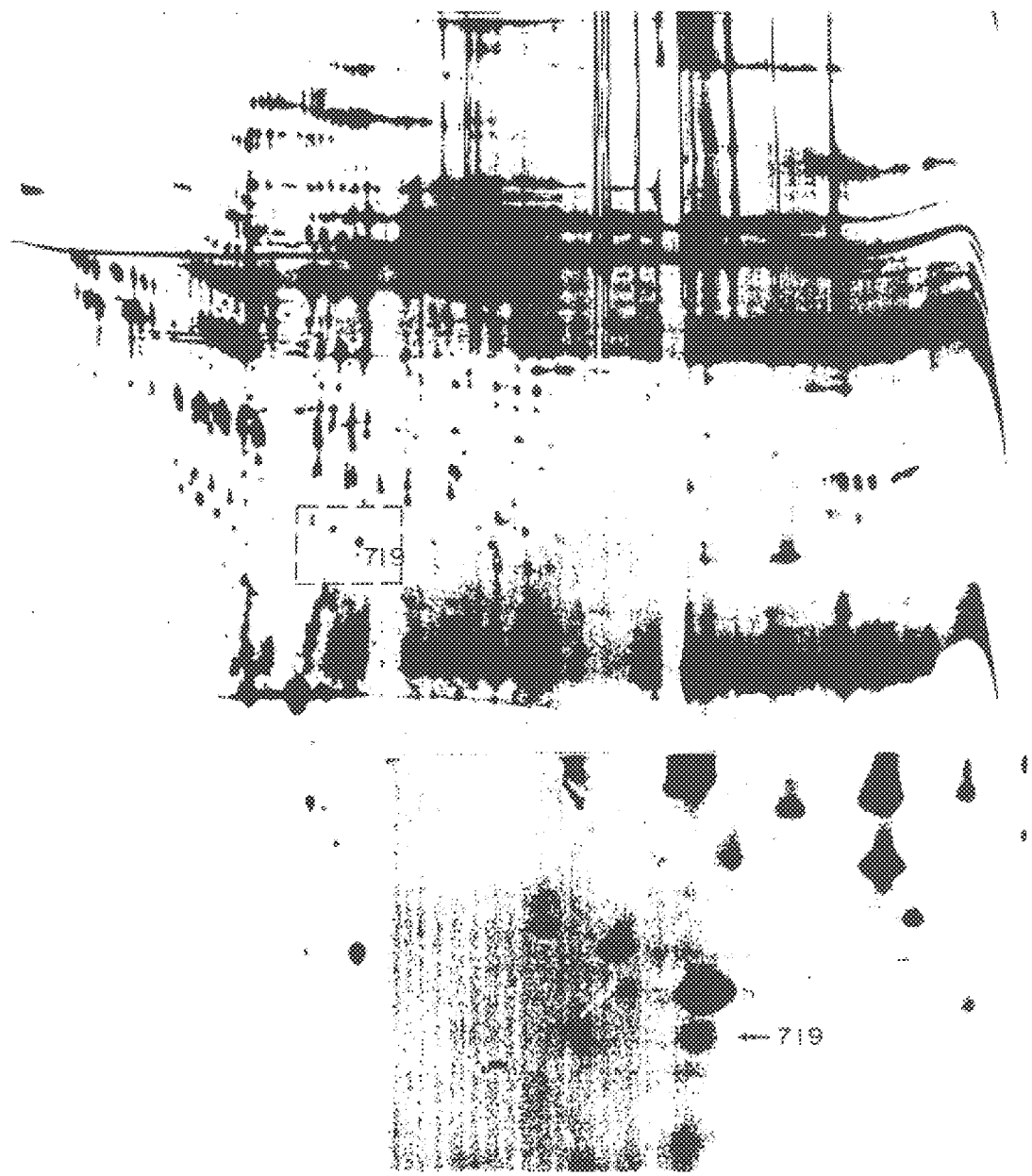

By comparing the above COS scores to the amount of protein 1318 in the gels, it was found that the protein designated 1318 displayed a correlation with pain severity. This is represented in FIG. 5.

The same comparison was made with proteins 1316, 1204, 1305, 3203 and 3211. Also a comparison was made with the average of proteins 1318 and 1316. These results are shown in FIGS. 6–11.

Using similar methods, a correlation may also be made with spot 719 and any of the conditions which result from peripheral nerve damage.

EXAMPLE 7

To examine the effectiveness of a course of treatment for conditions resulting from peripheral nerve damage, a blood sample would be obtained from a patient prior to the treatment. A two-dimensional gel or immunoassay would be run, stained and analyzed for levels of one or more of the proteins listed in Tables II, III,IV and V to obtain a baseline. After instituting treatment, one or more blood samples are taken from the patient and analyzed for levels of the same protein or proteins which were initially analyzed. A proportional increase or decrease to normal levels (depending on whether the protein analyzed is one which is found to increase or decrease in the patients) signifies that the treatment is successful.

EXAMPLE 8

A. Preparing Antigens. After two-dimensional gel electrophoresis is performed on a patient, for instance one with confirmed CLP, the gel would be stained with Coomassie blue in order to locate a protein of interest. The gel is rinsed with deionized water for a few minutes, changing the water several times. The spot containing a protein is cut out of the gel with a scalpel, and placed on a piece of parafilm or plastic wrap. The edge of a paper towel is used to remove by capillary action any standing water. Next, the plungers from the barrels of two 5 cc syringes are removed, and the gel piece is placed into one of the barrels. The plunger is then replaced and the syringe outlet is positioned in the barrel of the second syringe. Using rapid, firm pressure on the plunger, the gel is pushed into the barrel of the second syringe. This process is repeated several times back and forth between the two syringes. Then, 21-gauge needles are placed onto the outlet of the syringes, and the process is repeated. A small amount of buffer (PBS) may be necessary to keep the small fragments passing back and forth between the syringes. The samples are now ready for injection.

B. Preparing Antisera. Antibodies are raised in rabbits immunized by injecting the antigen preparation (above). An initial subcutaneous injection of approximately 150 ug of one of the protein preparations would be followed by two monthly injections of approximately 100 ug of the antigen. This will lead to a sufficient antibody titer for use in an immunoassay.

C. Preparing Monoclonals. Monoclonal antibodies may be prepared according to the method of KoZhler and Milstein. This method involves immunizing mice with an antigen bearing one or more epitopes (i.e., one of the lower back pain proteins). The mice develop spleen cells making anti-epitope(s) which appear as an antibody (or antibodies) in the serum. The spleen is removed and the individual cells fused in polyethylene glycol with constantly dividing (i.e., immortal) B-tumor cells selected for a purine enzyme deficiency and often for their inability to secrete Ig. The resulting cells are distributed into micro-well plates in HAT (hypoxanthine, aminopterin, thymidine) medium which kills off the perfusion partners, at such a high dilution that, on average, each well will contain less than one hybridoma cell. Each hybridoma being the fusion product of a single antibody-forming cell and a tumor cell will have the ability of the former to secrete a single species of antibody and the immortality of the latter enabling it to proliferate continuously, clonal progeny providing an unending supply of antibody.

The above described procedure was followed and antibody 10C11.1E7 was obtained. This antibody reacted with a protein with a molecular weight corresponding to spot 1bp13–14.719 in an immunoblot of a one dimensional gel. Antibody 10C11.1E7 was deposited at the American Type Culture Collection, 12301 Parklawn Drive, Rockville, Md. 20852, on Jun. 7, 1995, accession number HB11929.

D. Western Blot (Immunoblot). Proteins from the two-dimensional gels of Examples 1 and 2 may be electrophoretically eluted, prior to staining, to 0.2 um nitrocellulose membranes. The membranes are rinsed with PBS and incubated with BSA (3% BSA (fraction V, 0.02% sodium azide in PBS). The membranes are then incubated with primary rabbit polyclonal antibodies (obtainable by the above method) at a concentration of about between 1 and 50 ug/ml in PBS. The membranes are then washed with several changes of PBS, followed by incubation with goat anti-rabbit IgG labeled with horseradish peroxidase. Finally, after rinsing with PBS, the membranes are developed with 4-chloro-1-naphthol (stock solution is 0.3 g chloro-naphthol in 10 ml absolute ethanol; working solution is 0.1 ml stock added to 10 ml of 50 mM TRIS, pH 7.6; the white precipitate is filtered and 10 ul of 30% hydrogen peroxide is added). The reaction is stopped by rinsing with PBS. A positive result is seen if the spots of interest develop into a blue-black color.

In the foregoing immunoblot procedure, monoclonal antibodies may be substituted for the primary polyclonal antisera to obtain a higher specificity.

E. Radioimmunoassay (RIA). To perform this assay, one would use a monoclonal antibody to one of the proteins of interest (such as those exemplified in Examples 1 and 2), which would be prepared according to known methods as discussed above.

A sheet of nitrocellulose paper is cut to the size of a dot blot apparatus. The sheet is pre-wetted with water, and fitted onto the apparatus. A plasma sample from the patient is placed in the wells (30 ul/well) in serial dilutions, and incubated for two hours in a humid atmosphere. The sheet is then washed with two changes of PBS. The sheet is then blocked by incubating with a solution of 3% BSA/PBS with 0.02% sodium azide for at least 2 hours. Following washing with PBS, the primary monoclonal antibody (in a solution of 3% BSA/PBS with 0.02% sodium azide) is added at a suitable dilution and incubated for 2 hours with agitation. Unbound antibody is washed away with PBS. An $I^{125}$-labeled goat anti-rabbit IgG (in 3% BSA/PBS with 0.02% sodium azide) is then incubated with the sheet for about 2 hours with agitation. Unbound labeled antibody is removed by washing four times with PBS for 5 minutes each. The amount of bound labeled antibody is determined by autoradiographic detection. This is done by placing the sample sheet in direct contact with an X-ray film and storing this system at −70° C. with an intensifying screen. Results can be crudely quantitated by visual examination of the exposed film and more finely quantitatively by densitometric tracing. The relative amounts of antigen in different samples are determined by comparing midpoints of the titration curves. Absolute amounts of antigen can be determined by comparing these values with those obtained using known amounts of antigen.

F. Enzyme-linked Immunosorbent Assay (ELISA). This immunoassay is performed as set forth above in the RIA method; however, rather than the secondary antibody, goat anti-rabbit IgG, being labeled with $I^{125}$, it is labeled with horseradish peroxidase (HRP). In order to detect and quantify the HRP, the dot blot is developed with chloro-naphthol. 4-Chloro-1-naphthol (0.3 g) is dissolved in 10 ml of absolute ethanol to prepare a stock solution. Immediately prior to developing the assay, 0.1 ml of the stock is added to 10 ml of 50 mM TRIS (pH 7.6). The white precipitate formed is filtered with Whatman No. 1 filter paper. 10 ul of 30% $H_2O_2$ is added to the solution. The chloro-naphthol solution is added to the nitrocellulose sheet and agitated until the spots are suitably dark (about 30 min.). The reaction is stopped by rinsing with PBS. The results can be determined as with the RIA, and quantification performed by visual inspection or by reflection densitometry.

EXAMPLE 9

Typical test kits for use with RIA or ELISA tests will contain:

A

1. A plate with absorbed rabbit Fab fragment IgG (to any of the proteins set forth in Tables II, III, IV and V, preferably the protein of spot 1bp13–14.719), or nitrocellulose sheets with the absorbed rabbit IgG.

2. Rabbit whole IgG (to the same protein as above).

3. Labeled goat anti-rabbit IgG ($F_c$ portion).

B

1. Mouse monoclonal (to any of the proteins listed in Tables II, III, IV and V preferably the protein of spot 1bp13–14.719).

2. Labeled goat anti-mouse.

These kits may also contain appropriate buffers such as PBS, blocking solution, and appropriate enzyme substrates (for ELISAs). These materials may be provided with the kit or may be separately provided or prepared.

The term "plate" is used in the broad sense to include any flat surface which can be employed with an RIA or ELISA.

In practice the test kit A (above) would be employed as follows:

1. Incubate the plate with the serum of the patient under test for an appropriate time and temperature (e.g., from 2–4 hours at 37° C.).
2. Wash with BSA/PBS.
3. Incubate with rabbit whole IgG and wash with buffer.
4. Incubate with labeled goat anti-rabbit IgG ($F_c$ portion) and wash with the same buffer.
5. Detect the formation of a reaction product (or radioactive signal) in the case of a positive test by any of the aforementioned procedures.

The test kit B would be employed as follows:

1. Incubate a substrate (plate, nitrocellulose paper, etc.) with an unknown sample (such as plasma) for an appropriate time and temperature.
2. Wash with BSA/PBS.
3. Incubate substrate with the mouse monoclonal and wash with buffer.
4. Incubate with goat anti-rabbit IgG and wash with same buffer.
5. Detect the formation of a reaction product (or, radioactive signal) in the case of a positive test by an appropriate procedure.

We claim:

1. An antibody which specifically binds the protein derived from spot 1bp13–14.719, wherein said antibody is 10C11.1E7, ATCC HB11929.

2. A test kit for detecting peripheral nerve damage, comprising an antibody which specifically binds the protein derived from spot 1bp13–14.719; and a labeled antibody to said antibody, wherein said antibody which specifically binds the apo-E protein derived from spot 1bp13–14.719 is 10C11.1E7, ATCC HB11929.

* * * * *

UNITED STATES PATENT AND TRADEMARK OFFICE
CERTIFICATE OF CORRECTION

PATENT NO. : 5,844,097

DATED : December 1, 1998

INVENTOR(S) : Cameron et al.

It is certified that error appears in the above-identified patent and that said Letters Patent is hereby corrected as shown below:

Item [60], after "5,364,793" insert

--which is a continuation-in-part of application No. PCT/US91/08552, Nov. 15, 1991--, after "5,364,793", since Ser. No. 07/620,104 is already referred to, and in accordance with the present style for presentation/printing.

Signed and Sealed this

Fourteenth Day of December, 1999

Attest:

Q. TODD DICKINSON

Attesting Officer

Acting Commissioner of Patents and Trademarks